US010222335B2

(12) United States Patent
Stringari et al.

(10) Patent No.: US 10,222,335 B2
(45) Date of Patent: Mar. 5, 2019

(54) PHASOR METHOD TO FLUORESCENCE LIFETIME MICROSCOPY TO DISCRIMINATE METABOLIC STATE OF CELLS IN LIVING TISSUE

(75) Inventors: Chiara Stringari, Irvine, CA (US); Enrico Gratton, San Clemente, CA (US); Michelle Digman, Irvine, CA (US); Peter Donovan, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/283,356

(22) Filed: Oct. 27, 2011

(65) Prior Publication Data
US 2012/0276578 A1 Nov. 1, 2012

Related U.S. Application Data

(60) Provisional application No. 61/407,346, filed on Oct. 27, 2010.

(51) Int. Cl.
G01N 21/64 (2006.01)
(52) U.S. Cl.
CPC ..... *G01N 21/6486* (2013.01); *G01N 21/6408* (2013.01); *G01N 21/6458* (2013.01)
(58) Field of Classification Search
None
See application file for complete search history.

(56) References Cited

PUBLICATIONS

Golfetto O. Phasor Approach to Fluorescence Lifetime Image Microscopy to Measure Stem Cell Differentiation, PhD Thesis, published on Jul. 13, 2010, Padova Digital University, Italy, http://tesi.cab.unipd.it/25111/.*
Digman MA et al. The Phasor Approach to Fluorescence Lifetime Imaging Analysis, Biopys J: Biophysical Letters, 94: L14-16, 2008 and Supplemental material.*
Digman MA et al. The Phasor Approach to Fluorescence Lifetime Imaging Analysis, Biophys J: Biophysical Letters, 94: L14-16, 2008, Supplemental material.*
Carlson, "In vitro functional imaging in brain slices using fast voltage-sensitive dye imaging combined with whole-cell patch recording," Nature Protocols, vol. 3, p. 249-255, 2008.*
Caiolfa, "Monomer—dimer dynamics and distribution of GPI-anchored uPAR are determined by cell surface protein assemblies," J Cell Biology, vol. 179, p. 1067-1082, 2007.*
Berland, "Two-photon fluorescence correlation spectroscopy: method and application to the intracellular environment," Biophysical J, vol. 68, p. 694-701, 1995.*
Alcala, J. R., Gratton, E., Prendergast, F.G. (1987). "Fluorescence lifetime distribution in proteins." Biophys J. 51(4): 597-604.
Bel'Kov, M. V. B., S. L. (1990 ). "Fluorescence spectra and kinetics of isomers and dimers of retinoic acid." Journal of Applied Spectroscopy 53(6): 1271-1275.

Bornstein, P., Kang, A.H., Piez, K.A. (1966). "The nature and location of intramolecular cross-links in collagen." Proc Natl Acad Sci U S A 55(2):(2): 417-24.
Bowles, J., Knight, D., Smith, C., Wilhelm, D., Richman, J., Mamiya, S., Yashiro, K., Chawengsaksophak, K., Wilson, M.J., Rossant, J., Hamada, H., Koopman, P. (2006). "Retinoid signaling determines germ cell fate in mice." Science 312(5773): 596-600.
Brancaleon, L., Magennis, S.W., Samuel, I.D., Namdas, E., Lesar, A., Moseley, H. (2004). "Characterization of the photoproducts of protoporphyrin IX bound to human serum albumin and immunoglobulin" G. Biophys Chem. 109(3): 351-60.
Campagnola, P. J., Loew, L.M. (2003). "Second-harmonic imaging microscopy for visualizing biomolecular arrays in cells, tissues and organisms." Nat Biotechnol. 21(11): 1356-60.
Chia, T. H., Williamson, A., Spencer, D.D., Levene, M.J. (2008). "Multiphoton fluorescence lifetime imaging of intrinsic fluorescence in human and rat brain tissue reveals spatially distinct NADH binding." Opt Express. 16(6): 4237-49.
Cinquin, O., Crittenden, S.L., Morgan, D.E., Kimble (2010 ). "Progression from a stem cell-like state to early differentiation in the C. elegans germ line." Proc Natl Acad Sci U S A. 107(5): 2048-53.
Clayton, A. H., Hanley, Q.S., Verveer, P.J. (2004). "Graphical representation and multicomponent analysis of single-frequency fluorescence lifetime imaging microscopy data." J. Microsc. 213(Pt 1): 1-5.
Colyer, R., Lee, C., Gratton, E. (2008). "A novel fluorescence lifetime imaging system that optimizes photon efficiency." Microsc Res Tech. 71(3): 201-13.
Denk, W., Strickler, J.H., Webb, W,W. (1990). "Two-photon laser scanning fluorescence microscopy. ." Science 248 (4951): 73-6.
Digman, M. A., Caiolfa, V.R., Zamai, M., Gratton, E. (2008). "The phasor approach to fluorescence lifetime imaging analysis." Biophys J. 94(2): L14-6.
Durston, A. J., Timmermans, J.P., Hage, W.J., Hendriks, H.F., de Vries, N. J., Heideveld, M., Nieuwkoop, P.D. (1989). "Retinoic acid causes an anteroposterior transformation in the developing central nervous system." Nature 340(6229): 140-4.
Guo, H. W., Chen, C.T., Wei, Y.H., Lee, O.K., Gukassyan, V., Kao, F.J., Wang, H.W. (2008). "Reduced nicotinamide adenine dinucleotide fluorescence lifetime separates human mesenchymal stem cells from differentiated progenies." J Biomed Opt. 13(3): 050505.

(Continued)

*Primary Examiner* — G Steven Vanni
(74) *Attorney, Agent, or Firm* — Brooks Kushman P.C.

(57) ABSTRACT

A label-free imaging method to monitor stem cell metabolism discriminates different states of stem cell as they differentiate in a living tissues. We use intrinsic fluorescence biomarkers and the phasor approach to Fluorescence Lifetime Imaging Microscopy (FLIM). We identify and map intrinsic fluorophores such as collagen, retinol, retinoic acid, flavins, nicotinamide adenine dinucleotide (NADH) and porphyrin. We measure the phasor values of germ cells in *C. Elegans* germ line. Their metabolic fingerprint cluster according to their differentiation state, reflecting changes in FAD concentration and NADH binding during the differentiation pathway. The phasor approach to lifetime imaging provides a label-free, fit-free and sensitive method to identify different metabolic state of cells during differentiation, to sense small changes in the redox state of cells and may identify symmetric and asymmetric divisions and predict cell fate.

8 Claims, 20 Drawing Sheets
(20 of 20 Drawing Sheet(s) Filed in Color)

(56) References Cited

PUBLICATIONS

Helmchen, F., Denk, W. (2005). "Deep tissue two-photon microscopy." Nat Methods. 2(12): 932-40.

Hess, S. T., Sheets, E.D., Wagenknecht-Wiesner, A., Heikal, A.A. (2003). "Quantitative analysis of the fluorescence properties of intrinsically fluorescent proteins in living cells. ." Biophys J. 85(4): 2566-80.

Huang, S., Heikal, A.A., Webb, W.W. (2002). "Two-photon fluorescence spectroscopy and microscopy of NAD(P)H and flavoprotein." Biophys J. 82(5): 2811-2825.

Jameson, D. M., Gratton., E., Hall, R. D. (1984). "The Measurement and Analysis of Heterogeneous Emissions by Multifrequency Phase and Modulation Fluorometry." Applied Spectroscopy Reviews 20(1): 55-106.

König, K., Riemann, I. (2003). "High-resolution multiphoton tomography of human skin with subcellular spatial resolution and picosecond time resolution." J Biomed Opt. 8(3): 432-9.

König, K., Uchugonova, A., Gorjup, E. (2010). "Multiphoton fluorescence lifetime imaging of 3D-stem cell spheroids during differentiation . ." Microscopy Research and Technique 00: 000-000.

Lakowicz, J. R., Szmacinski, H., Nowaczyk, K., Johnson, M.L. (1992). "Fluorescence lifetime imaging of free and protein-bound NADH." Proc Natl Acad Sci U S A. 89(4): 1271-5.

Lin, Y., Gill, M.E., Koubova, J., Page, D.C. (2008). "Germ cell-intrinsic and -extrinsic factors govern meiotic initiation in mouse embryos." Science 322(5908): 1685-7.

Lonergan, T., Brenner, C., Bavister, B. (2006). "Differentiation-related changes in mitochondrial properties as indicators of stem cell competence." J Cell Physiol. 208(1): 149-53.

Medine, C. N., McDonald, A., Bergmann, A., Duncan, R.R. (2007). "Time-correlated single photon counting FLIM: some considerations for physiologists." Microsc Res Tech. 70(5): 420-5.

Parker, G. C., Acsadi, G., Brenner, C.A. (2009). "Mitochondria: determinants of stem cell fate? ." Stem Cells Dev. 18(6): 803-6.

Pelet, S., Previte, M.J., Laiho, L.H., So, P.T. (2004). "A fast global fitting algorithm for fluorescence lifetime imaging microscopy based on image segmentation. ." Biophys J. 87(4): 2807-17.

Peter, M., Ameer-Beg, S.M. (2004). "Imaging molecular interactions by multiphoton FLIM." Biol Cell. 96(3): 231-6.

Redford; G. I., Clegg, R.M. (2005). "Polar plot representation for frequency-domain analysis of fluorescence lifetimes." J. Fluoresc. 15(5): 805-15.

Schneckenburger, H., Wagner, M., Weber, P., Strauss, W.S., Sailer, R. (2004). "Autofluorescence lifetime imaging of cultivated cells using a UV picosecond laser diode." J Fluoresc. 14(5): 649-54.

Skala, M. C., Riching, K.M., Gendron-Fitzpatrick, A., Eickhoff, J., Eliceiri, K.W., White, J.G., Ramanujam, N. (2007). "In vivo multiphoton microscopy of NADH and FAD redox states, fluorescence lifetimes, and cellular morphology in precancerous epithelia." Proc Natl Acad Sci U S A 104(49): 19494-9.

Smith, J., Ladi, E., Mayer-Proschel, M., Noble, M. (2000). "Redox state is a central modulator of the balance between self-renewal and differentiation in a dividing glial precursor cell." Proc Natl Acad Sci U S A 97(18): 10032-7.

Squirrell, J. M., Wokosin, D.L., White, J.G., Bavister, B.D. (1999). "Long-term two-photon fluorescence imaging of mammalian embryos without compromising viability." Nat Biotechnol. 17(8): 763-7.

Uchugonova, A., König, K. (2008). "Two-photon autofluorescence and second-harmonic imaging of adult stem cells." J Biomed Opt. 13(5): 054068.

Verveer, P. J., Squire, A., Bastiaens, P.I. (2000). "Global analysis of fluorescence lifetime imaging microscopy data." Biophys J. 78(2127-37).

Wouters, F. S., Verveer, P.J., Bastiaens, P.I. (2001). "Imaging biochemistry inside cells." Trends Cell Biol. 11(5): 203-11.

Zipfel, W. R., Williams, R.M., Christie, R., Nikitin, A.Y., Hyman, B.T., Webb, W.W. (2003). "Live tissue intrinsic emission microscopy using multiphoton-excited native fluorescence and second harmonic generation." Proc Natl Acad Sci U S A 100(12): 7075-80.

Zipfel, W. R., Williams, R.M., Webb, W.W. (2003). "Nonlinear magic: multiphoton microscopy in the biosciences." Nat Biotechnol. 21(11): 1369-77.

Becker, W., Bergmann, A., Hink, M.A., König, K., Benndorf, K., Biskup, C. (2004). "Fluorescence lifetime imaging by time-correlated single-photon counting. ." Microsc Res Tech. 63(1): 58-66.

Chorvat, D., Jr., Chorvatova, A. (2009). "Multi-wavelength fluorescence lifetime spectroscopy: a new approach to the study of endogenous fluorescence in living cells and tissues." Laser Physics Letters 6(3): 175-193.

Dabir, A., Trivedi, CA., Ryu, Y., Pande, P., Jo, JA. (2009). "Fully automated deconvolution method for on-line analysis of time-resolved fluorescence spectroscopy data based on an iterative Laguerre expansion technique." J Biomed Opt 14(2): :024030.

Fu , Ng, BK, Razul, SG. (2009). "Fluorescence lifetime discrimination using expectation-maximization algorithm with joint deconvolution." J Biomed Opt. 14(6): 064009.

Jo, J. A., Fang, Q., Papaioannou, T., Marcu, L. (2004). "Fast model-free deconvolution of fluorescence decay for analysis of biological systems." Journal of Biomedical Optics 9(4): 743-752.

Lee, K., Siegel, J, Webb, SE, Lévêque-Fort, S, Cole, MJ, Jones, R, Dowling, K, Lever, MJ, French, PM. (2001). "Application of the stretched exponential function to fluorescence lifetime imaging." Biophys J. 81(3): 1265-74.

Munro, I., McGinty, J, Galletly, N, Requejo-Isidro, J, Lanigan, PM, Elson, DS, Dunsby, C, Neil, MA, Lever, MJ, Stamp, GW, French, PM. (2005). "Toward the clinical application of time-domain fluorescence lifetime imaging." J Biomed Opt. 10(5): 051403.

Siegel J, E. D., Webb SE, Lee KC, Vlandas A, Gambaruto GL, Lévêque-Fort S, Lever MJ, Tadrous PJ, Stamp GW, Wallace AL, Sandison A, Watson TF, Alvarez F, French PM. (2003). "Studying biological tissue with fluorescence lifetime imaging: microscopy, endoscopy, and complex decay profiles." Appl Opt. 42(16): 2995-3004.

Stringari, C., et al., Phasor approach to fluorescence lifetime microscopy distinguishes different metabolic states of germ cells in a live tissue, Proc Natl Acad Sci USA (2011) 108(33), 13582-13587.

* cited by examiner

PHASOR METHOD TO FLUORESCENCE LIFETIME MICROSCOPY TO DISCRIMINATE METABOLIC STATE OF CELLS IN LIVING TISSUE

CROSS-REFERENCE TO RELATED APPLICATIONS

This application claims the benefit of Provisional Patent Application No. 61/407,346, filed on Oct. 27, 2010, which is incorporated by reference herein in its entirety.

SPONSORED RESEARCH AND DEVELOPMENT

This invention was made with government support under Grant Nos. GM076516; HD047675, HD049488; and RR003155 awarded by the National Institutes of Health. The government has certain rights in the invention.

FIELD OF THE INVENTION

The invention relates generally to methods used to detect the tissue/cell components. More particularly, it relates to the use of the Phasor method to discriminate the metabolic state of cells in living tissue.

BACKGROUND OF THE INVENTION

Multi-photon microscopy is suitable for high resolution and long term imaging of living tissues. It allows investigation of local environment in femtoliter volumes deep in tissues, thanks to its intrinsic three-dimensional resolution, high penetration depth, negligible out-of-focus photobleaching and (Helmchen 2005). minimal photo damage and phototoxicity (Denk 1990; Squirrell 1999; Zipfel 2003; Zipfel 2003). Auto-fluorescence in live tissues arises from endogenous proteins and physiologically relevant fluorophores such as collagen, elastin, porphyrin, retinoids, flavins, nicotinamide adenine dinucleotide, hemoglobin and serotonin (Zipfel 2003). NADH and FAD are the main metabolic coenzymes involved in oxidative phosphorylation and glycolysis and they report on metabolic changes associated with cell carcinogenesis and differentiation (Smith 2000; Skala 2007) while retinoid signaling is involved in differentiation of stem and precursor cells and embryonic development (Durston 1989; Bowles 2006). Two-photon excited fluorescence alone cannot assign auto-fluorescence signal to specific intrinsic molecular sources.

Additional methods have been proposed to assign auto-fluorescence to specific tissue components, but with limited success. Principal component analysis of emission spectra requires additional information on the tissue biochemical composition and can only separate a limited number of tissue components. The discrimination between intrinsic fluorescence sources by emission wavelength is also limited by the overlapping of emission spectra of different fluorescent species, such as NADPH and NADH (Huang 2002). Multi-exponential fitting of complex fluorescence intensity decays is based on a fitting procedure that requires assumptions on the biological tissues, where multiple fluorescent species are present in the focal volume. Several fluorophores and proteins are characterized by conformational heterogeneity and have complex lifetime distribution with more than one exponential component (Alcala 1987; Wouters 2001; Peter 2004). Moreover non-exponential processes such as energy transfer (FRET), pH variation, scattering and quenching often occur in tissues. Hence the choice of a decay model for the intensity decay fitting is arbitrary and it difficult to associate specific tissue components to exponential decays (Verveer 2000; Pelet 2004; Medine 2007).

BRIEF SUMMARY OF THE INVENTION

We used the phasor approach to fluorescence lifetime microscopy (Jameson 1984; Digman 2008) which allows a straightforward interpretation of intrinsic fluorescence signal from living tissues directly in terms of physiological relevant fluorophores. We provide images of fluorescent species based on their decay properties rather than resolving the lifetimes of molecular species.

We separated multiple tissue components by cluster analysis of the phasor distribution in FLIM images from seminiferous tubules of a mice testis expressing Oct4 GFP transgene. GFP is expressed in undifferentiated germ cells, since Oct4 is a pluripotent stem cell marker (Chambers 2009). Each fluorescent molecular source is identified by its specific location in the phasor plot. We identified GFP, collagen, FAD, free and bound NADH, retinol and retinoic acid within the living tissue by using the pure species phasor locations. We observed that different compartments of the colon an small intestine tissue are defined by unique Phasor FLIM signatures. We can distinguish collagen fibers at the base of the crypts, the lamina propria, the vascular network and the epithelium. We measured the metabolic state of germ cells in the C. Elegans germ line by averaging the phasor distribution of a single cell in the tissue. C. Elegans germ line provides a genetically defined model for studying the progression from stem cell self renewal to differentiation (Hubbard 2007; Cinquin 2009; Cinquin 2010). Here we identified different metabolic fingerprints of stem cells during differentiation. We identified the epithelial stem cells at the base of the small intestine crypts. We performed 3D phasor FLIM metabolic mapping of the small intestine and colon crypts to measure and map the redox ratio of cells during differentiation in vivo.

We separated multiple tissue components by cluster analysis of the phasor distribution in FLIM images from seminiferous tubules of a mice testis expressing Oct4 GFP transgene. GFP is expressed in undifferentiated germ cells, since Oct4 is a pluripotent stem cell marker (Chambers 2009). Each fluorescent molecular source is identified by its specific location in the phasor plot. We identify GFP, collagen, FAD, free and bound NADH, retinol and retinoic acid within the living tissue by using the pure species phasor locations. We observed that different compartments of the colon an small intestine tissue are defined by unique Phasor FLIM signatures. We can distinguish collagen fibers at the base of the crypts, the lamina propria, the vascular network and the epithelium. We measured the metabolic state of germ cells in the C. Elegans germ line by averaging the phasor distribution of a single cell in the tissue. C. Elegans germ line provides a genetically defined model for studying the progression from stem cell self renewal to differentiation (Hubbard 2007; Cinquin 2009; Cinquin 2010). Here we identified different metabolic fingerprints of stem cells during differentiation. We identified the epithelial stem cells at the base of the small intestine crypts. We performed 3D phasor FLIM metabolic mapping of the small intestine and colon crypts to measure and map the redox ratio of cells during differentiation in vivo.

We monitored the metabolic signature of colon cancer cells over one entire week to study the relationship between Wnt signaling and metabolism. We now show that the induction of the transcription factor dominant negative 1 (dnLEF1) in colon cancer inhibits the colon cancer cell phenotype by shifting the metabolism from glycolysis to oxidative phosphorilation.

We identified two optical biomarkers to define the differentiation status of human embryonic stem cells (hESCs): NADH and lipid droplet-associated granules (LDAGs). During early hESC differentiation we now show that NADH concentrations increase, while the concentration of LDAGs decrease.

Single cell phasor FLIM signatures revealed an increased heterogeneity in the metabolic states of differentiating H9 and H1 hESC colonies.

We now demonstrate that by measuring the metabolic activity and redox ratio of cells by Phasor Fluorescence Lifetime Microscopy it is possible to predict the commitment of stem cells to different neuronal differentiation pathways, independent of the expression of lineage marker expression profiles.

In one embodiment, a method for to discriminate the in vivo metabolic state of cells in a tissue is provided comprising providing a tissue sample comprising a plurality of tissue components; performing fluorescence lifetime imaging microscopy to said tissue sample to generate a fluorescence lifetime imaging data of said tissue; and performing image segmentation to measure the average phasor value of regions of interest in the tissues, whereby the relative concentration of the tissue components are determined.

In a more particular embodiment the tissue is living.

In yet another embodiment the method is non-invasive and performed without the use of fitting exponentials.

In another embodiment of the method the method further comprises measuring the relative concentrations of fluorophores and mapping their spatial distribution in living tissues.

In another embodiment the method further comprising performing multi-harmonic analysis of the fluorescence lifetime imaging data with higher harmonics of the laser repetition rate, wherein the harmonics are $\omega = n\omega_o$ with n=2, 3, to separate tissue components having the same phasor location but with different lifetime distributions.

In another embodiment each tissue component has a specific location in the phasor plot that is determined by the intrinsic characteristics of its fluorescence decay.

In another embodiment every location in the phasor plot corresponds to specific regions of the cells or the living tissue.

In one embodiment, an apparatus for discriminating the metabolic state of cells in a tissue is provided comprising means for exciting endogenous proteins within a tissue to generate a fluorescence lifetime imaging data; and a computer programmed to perform image segmentation to measure the average phasor value of regions of interest in the tissues.

In one embodiment, a computer program product for tissue or cell analysis is provided, comprising: a computer-readable medium comprising: code for receiving a signal from a fluorescence lifetime imaging microscope apparatus, code for performing image segmentation on said signal to measure the average phasor value of regions of interest in the tissue.

In another embodiment, the product of the previous paragraph further comprising code for calculating the relative concentration and average phasor values of cells and region of interest.

Tissues or tissue samples utilized can be, but not limited to, stem cells, differentiated cells, cells undergoing symmetric division, cells undergoing asymmetric division, and undifferentiated germ cells, embryonic stem cells, induced pluripotent stem cells, cancer and precancer cells. Any type of cells can be used to look at metabolic changes during progression of diseases, pathologies, apoptosis and oxidative stress.

Tissue components can be, but not limited to, GFP, Oct4, collagen, FAD, NADH, retinol and retinoic acid; other intrinsic fluorophores such as melanin, porphyrin, keratins, collagen, elastin, folic acid, and hemoglobin (see the following reference for other examples of tissue components that can be analyzed: Zipfel, W. R., Williams, R. M., Christie, R., Nikitin, A. Y., Hyman, B. T., Webb, W. W., Live tissue intrinsic emission microscopy using multiphoton-excited native fluorescence and second harmonic generation. Proc Natl Acad Sci USA, 2003. 100(12): p. 7075-80—which is hereby incorporated by reference in its entirety).

More generally, the tissue components can be any tissue/cellular protein capable of emitting fluorescence upon exciting with photons or capable of auto-fluorescence. Such tissue/cellular proteins can also include metabolic enzymes and stem cell and non-stem cell conventional markers known to those of skill in the art.

This method is a promising non-invasive optical tool for monitoring metabolic pathways during differentiation or disease progression, and for cell sorting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present invention, reference is now made to the following descriptions taken in conjunction with the accompanying drawing, in which.

Here fluorescence intensity image of a *C. elegans* germ line (a) excited at 740 nm and (b) excited at 880 nm. Histone-GFP fusion protein allows us to identify the position and differentiation state of the germ cells that are indicated with different colors: distal mitotic region (blue), proximal mitotic region (red), transition zone (green), and meiotic pachytene (cyan). A red cursor of 5 μm diameter selects the region of interest of a germ cell in the intensity image at (c) 880 nm and (d) 740 nm. (e) Phasor plot of the FLIM image excited at 740 nm (the color scale is the same to the one in FIG. 1d). (f) Scatter plot of the cell phasor of all germ cells excited at 740 nm. Every cell phasor (squares) is represented with a color that corresponds to its differentiation state in FIG. 4b. The distribution of distal mitotic cells in blue (blue, N=14), proximal mitotic region (red, N=20), transition zone cells (green, N=83) are clearly separated. The mean values of clusters are represented by the colored stars, while the standard deviation by the dotted lines. (g) Scatter plot of the mean values of cell phasor distributions in distal mitotic region (blue), proximal mitotic region (red) and transition zone (green) for N=6 independent *C. elegans* germ line. The independent samples are represented with different symbols. (h) Scatter plot of the mean values of the cell phasor distributions for N=6 independent germ lines. Each sample is translated in the phasor plot as to make all the distal mitotic region value coincident. The standard deviations of the proximal mitotic region and transition zone are represented by the dotted lines. (i) Zoomed image of the mitotic region of the *C. elegans* germ line excited at 880 nm in FIG. 4b. Cells are numbered in a distal to proximal direction. Blue cells belong to the distal mitotic region, while red cells belong to the proximal mitotic region. (l) Scatter plot of the phasor average values of the 20 germ cells indicated in FIG. 4i.

Figure 5:
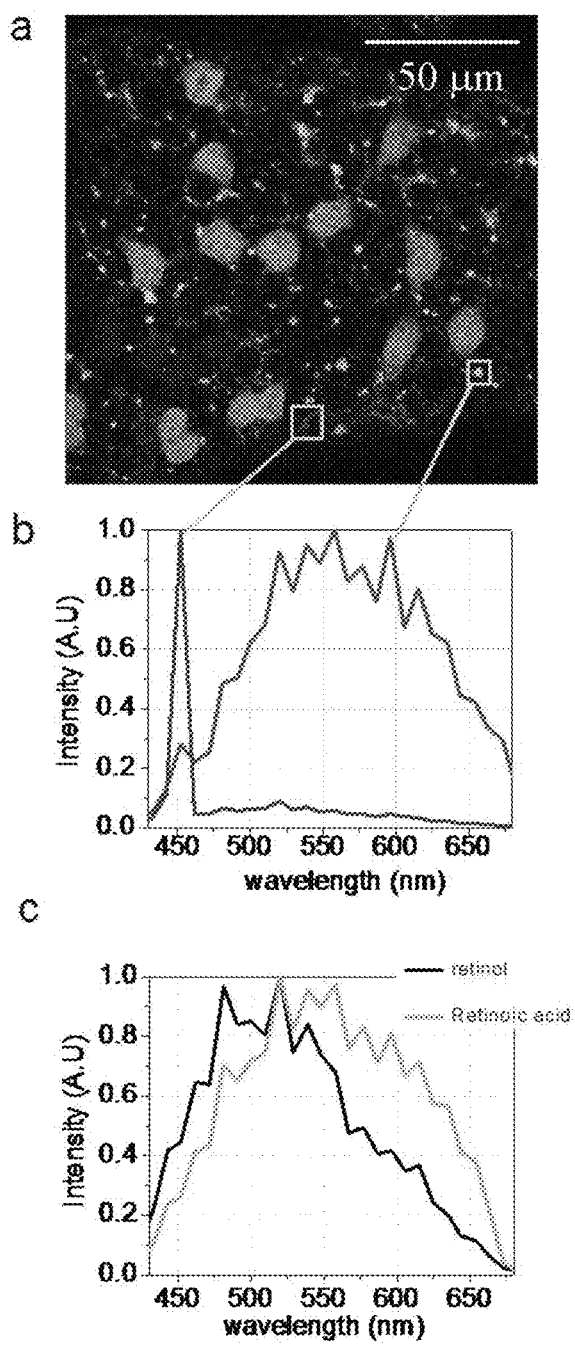

FIG. 5 (SM1) shows a spectral image of seminiferous tubule. (a). Spectral image excited at 900 nm of the same field of view of the FLIM image of FIG. 2. The colors of the image are spectrally coded. The blue pixels correspond to the SHG signal acquired at 450 nm. Three different regions of interest are selected by numbered squares. (b) Emission spectra measured in two regions of interest. (c). Emission spectra measured from pure retinol and retinoic acid.

Figure 6:
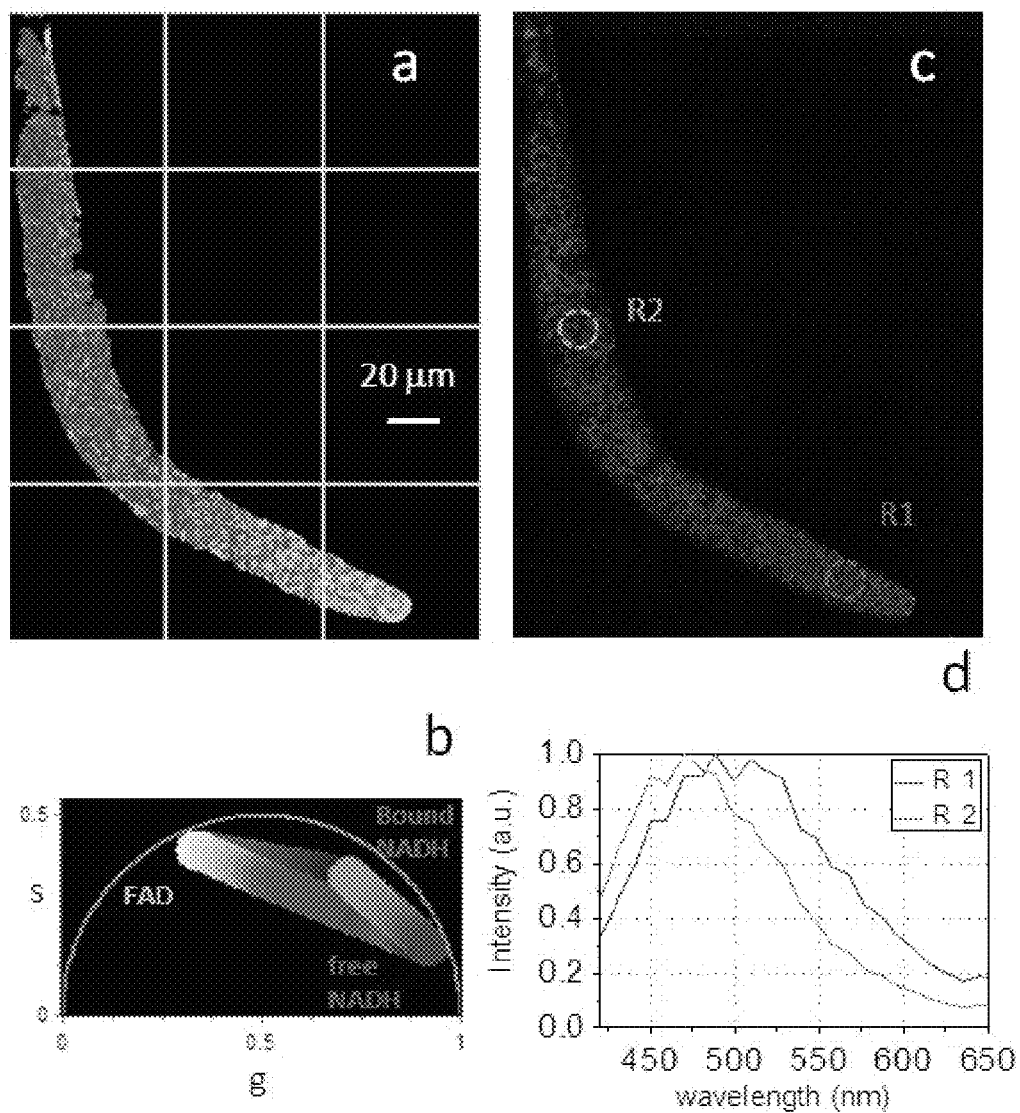

FIG. 6 (SM2) Shows the metabolites gradients in *C. Elegans* Germ line (a) Phasor color map of the relative concentrations of FAD (red), Free NADH (blue) and NADH bound to Malate dehydrogenase (MDH) (green) in the same *C. Elegans* germ line of FIG. 4a that is excited at 740 nm. Pixels in the images are highlighted with the same color scale used in the phasor plot of FIG. SM2.b. (b) Phasor plot selection using linear cluster that represent all possible relative concentrations of pure FAD (red), Free NADH (blue) and NADH bound to MDH (green). (c) Spectral image excited at 740 nm of the same field of view of C. Elegans germline of FIG. 4.a. The colors of the image are spectrally coded. The region of interest R1 is selected in the mitotic region while the region of interest R2 is selected in the transition zone of the germline. (d) Emission spectra measured in two regions of interest R1 and R2. The emission spectrum of R1 has a peak at 500 nm, while the R2 emission spectrum has a peak at 450 nm. The blue shift of the spectrum indicates an increase in bound NADH with respect to free NADH during differentiation.

Figure 7:
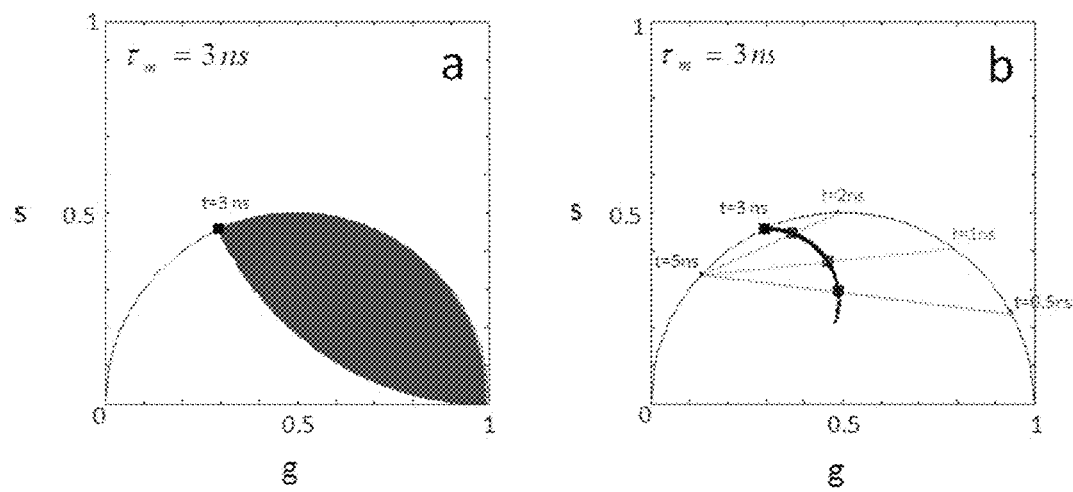

FIG. 7 (SM3) shows the resolving power of the phasor plot with respect to average lifetime and classical multi-exponential fitting. (a) The blue area in the phasor plot represent all possible combinations of two single lifetimes components t1 and t2 that give rise to an average lifetime $\tau_m = f_1 t_1 + f_2 t_2$ of 3 ns, i.e. the same average lifetime can be obtained with different combination of two components. Instead the phasor representation can separate tissue components with the same average lifetime but that are characterized by different lifetime distributions. (b) Three molecular species with average lifetime of 3 ns are represented in the phasor plot. The red species has 5 ns and 2 ns component, the green species 5 ns and 1 ns and the blue species 5 ns and 0.5 ns. The 5 ns exponential component is common to all three species. If you want to resolve a mixture of these molecular species by the classical multi-exponential fitting it is impossible to assign the fractional intensity of the 5 ns exponential to any specific species.

Figure 8:
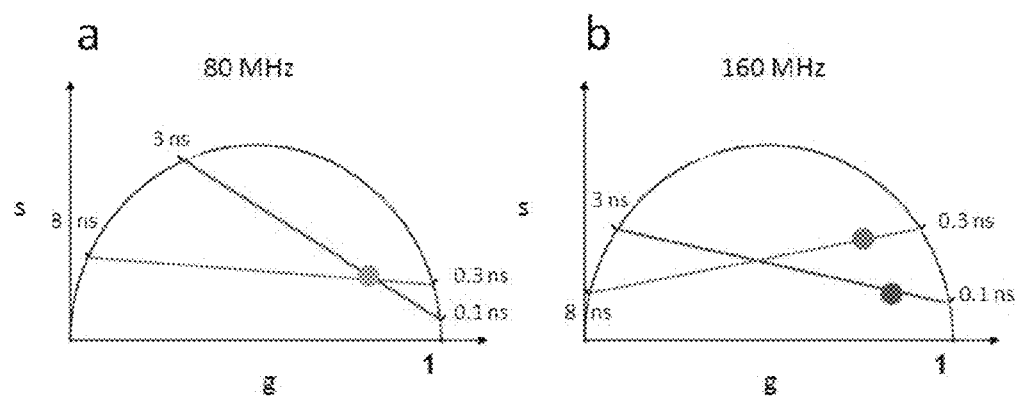

FIG. 8 (SM4) shows Multi-harmonic phasor representation (a) Phasor plot at the first harmonic, (80 MHz). The gray spot in the plot represents two points with two different lifetime distributions. One is a linear combination of 0.1 ns and 3 ns and the other is a linear combination of 0.3 ns and 8 ns. (b). Phasor plot at the second harmonic, i.e at 160 MHz. The same points with the same combination of lifetime are here represented. The point that is a linear combination of 0.1 ns and 3 ns is represented in red, while the one which is linear combination of 0.3 ns and 8 ns is represented in blue.

Figure 9:
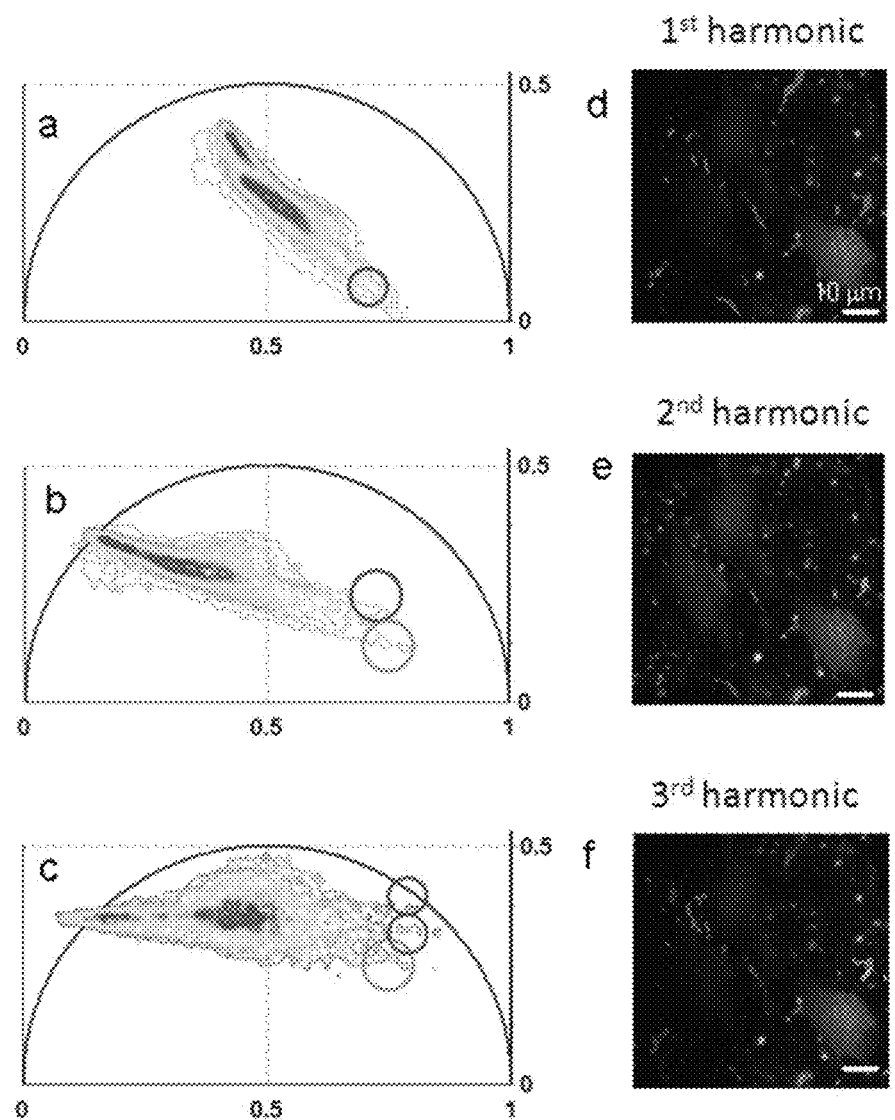

FIG. 9 (SM5) shows Multi-harmonic phasor analysis separates different lifetime distribution in living tissue. (a) Phasor plot of the FLIM images above calculated at the $1^{st}$ harmonic. The red color selects the collagen phasor cluster. (b) Phasor plot of the same FLIM images calculated at the $2^{nd}$ harmonic. The phasor distribution has two separated clusters selected by the red and the green colors. (c) Phasor plot of the same FLIM images calculated at the $3^{nd}$ harmonic. The phasor distribution has three separated clusters selected by the red, the green and the blue colors. (d-f) Phasor color maps of the FLIM images analyzed with the $1^{st}$ harmonic (d), $2^{nd}$ harmonic (e) and $3^{rd}$ harmonic (f). Pixel are highlighted with the same color corresponding to the clusters in plot (a-c)

Figure 10:
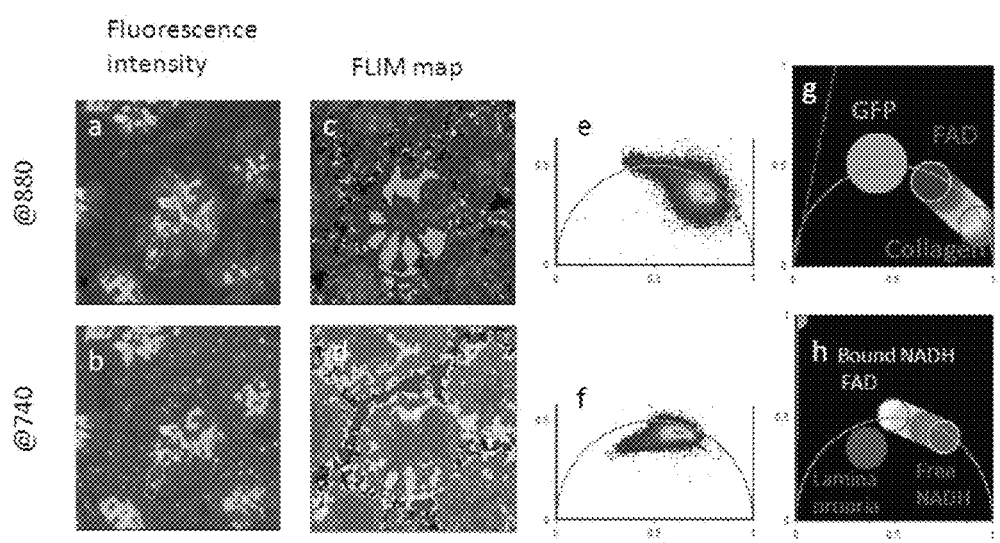

FIG. 10 shows how Phasor FLIM identifies stem cells in the small intestine crypt. Two-photon fluorescence intensity image excited at 880 nm (a) and 740 (b) of one crypt of the small intestine of a Lgr5-GFP mice that expresses GFP in the stem cells. (c) Phasor color maps at 880 nm of the relative concentrations of FAD (blue), collanen (orange) and GFP (green). (d) Phasor color maps at 740 nm of the relative concentrations of free NADH (purple) and bound NADH (cyan-white) and lamina propria (blue). Purple color indicates a high free/bound NADH ratio, while violet, cyan and white indicate linearly and progressively decreasing ratios free/bound NADH ratio. (e-f) FLIM phasor histogram of the FLIM image excited at 880 nm (e) and 740 nm (f). (g-h) Phasor plot selection using linear cluster that represent all possible relative concentrations of pure FAD (blue), Free NADH (purple) and bound NADH (white), GFP (green), collagen (orange).

Figure 11:
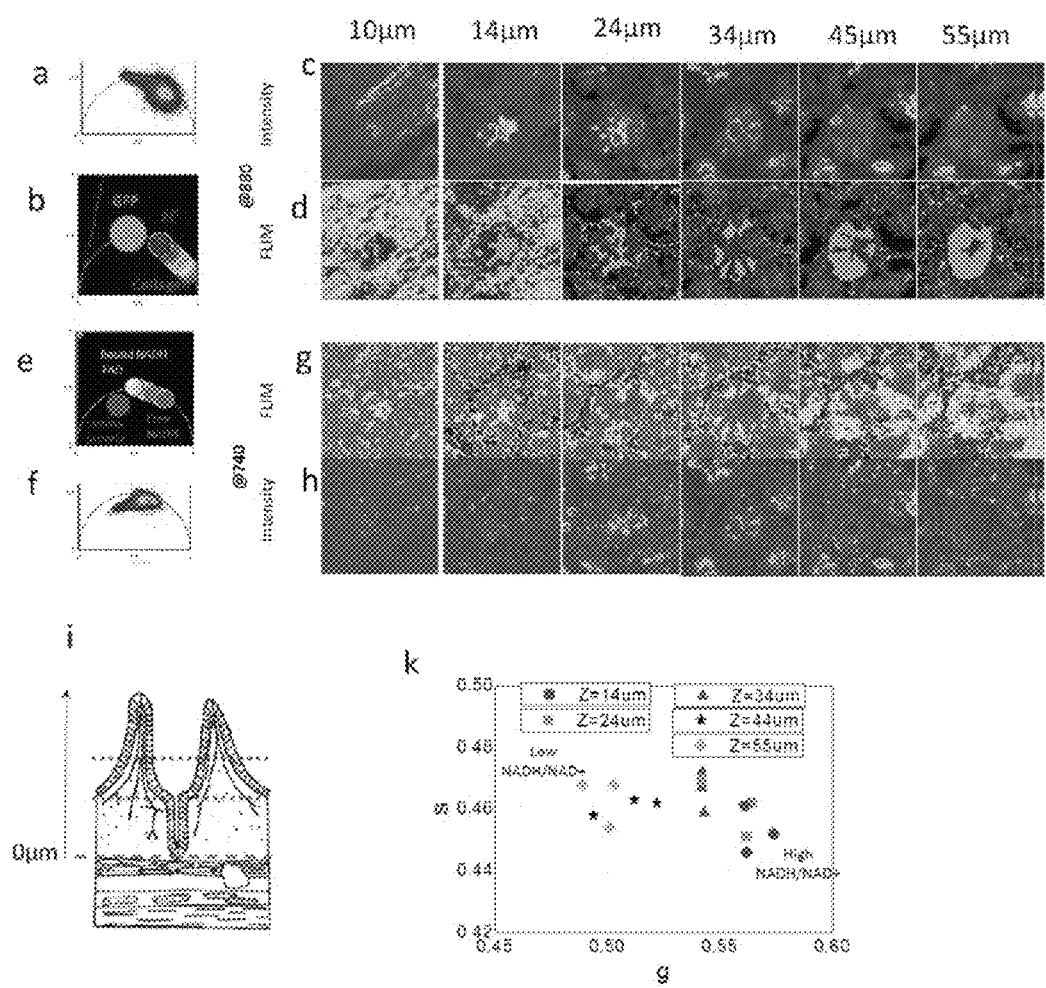

FIG. 11 shows a 3D Phasor FLIM reconstruction of the small intestine crypt from a Lgr5-GFP mice that expresses GFP in the stem cells. (a) FLIM phasor histogram of the FLIM images excited at 880 nm (b) Phasor plot selection using linear cluster that represent all possible relative concentrations of pure GFP (green), FAD (blue) and collagen (orange). (c) Two-photon fluorescence intensity images excited at 880 nm at different depth. (d) Phasor color maps at 880 nm of the relative concentrations of FAD (blue), collanen (orange) and GFP (green). (e) Phasor plot selection using linear cluster that represent all possible relative concentrations of lamina propria (blue), pure Free NADH (purple) and bound NADH (white). Purple color indicates a high free/bound NADH ratio, while violet, cyan and white indicate linearly and progressively decreasing ratios free/bound NADH ratio. (f) FLIM phasor histogram of the FLIM images excited at 740 nm. (g) Phasor color maps at 740 nm of the relative concentrations of free NADH (purple) and bound NADH (cyan-white) and lamina propria (blue). (h) Two-photon fluorescence intensity images excited at 740 nm at different depth. (i) schematic morphology of the small intestine. (k) Scatter plot of the mean values of the stem cell phasor signature at different depths. (cyan diamond for Z=55 μm, black stars for Z=44 μm, red triangles for Z=34 μm, green squares for Z=24 μm and blue circles for Z=14 μm). Along the Z the stem cell phasor shifts toward the longer lifetime indicating an increase of bound NADH with respect to free NADH. i.e. an decrease in NADH/NAD+ ratio.

Figure 12:
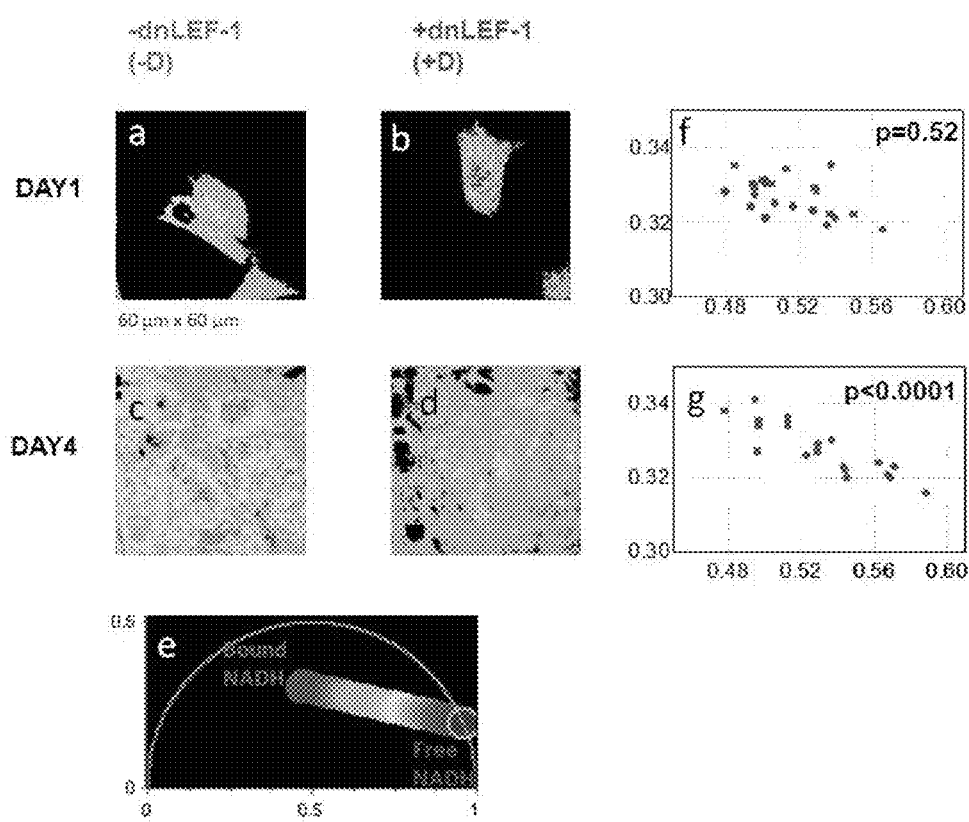

FIG. 12 shows that dnLEF-1 inhibits colon cancer cell phenotype and shift the metabolism from glycolysis to oxidative phosphorylation. (a-d) Phasor color maps of colon cancer cells excited at 740 nm shows relative concentrations of free NADH (red) and bound NADH (blue) at day 1 and day 4. Colon cancer cells DLD1 TR7 cells with (b,d) and without (a,c) the expression of dominant negative LEF-1 (dnLEF-1) (b,d). (e) Phasor plot selection using linear cluster that represent all possible relative concentrations of pure Free NADH (red) and bound NADH (blue). Red color indicates a high free/bound NADH ratio, while orange, yellow, green, cyan and blue indicate linearly and progressively decreasing ratios free/bound NADH ratio. (f-g) Scatter plot of the mean values of the phasor signature of the colon cancer cells with (red squares) and without (green circles) dnLEF-1 expression. At day 1 (f) and at day 4 (g).

Figure 13:
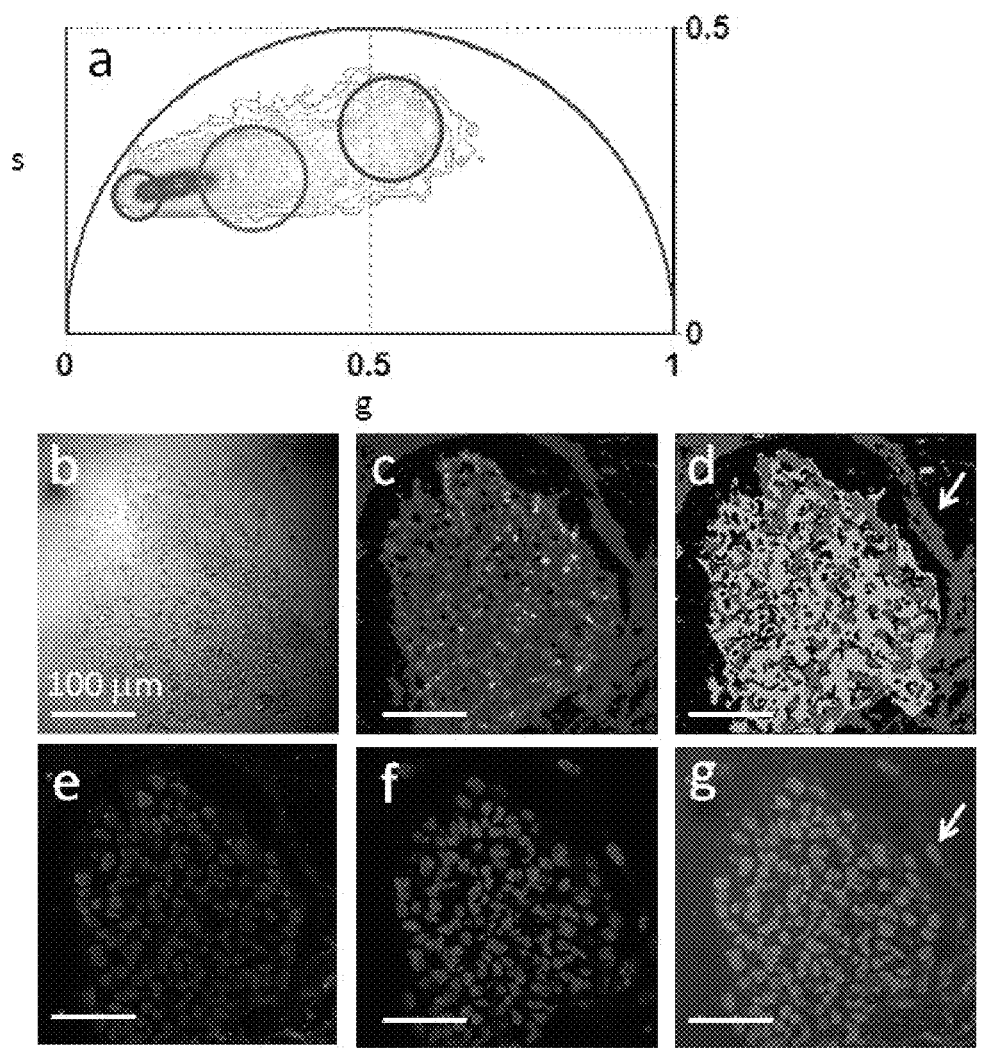

FIG. 13 shows label free identification of hESCs. (a) FLIM phasor histogram of the FLIM image excited at 760 nm from one H9 hESC colony co-cultured with Mouse embryonic fibroblasts (MEFs). The color scale (from blue to purple) corresponds to the 64 levels of the contours that indicate the percent occurrence in the phasor histogram of the pixels of the image. Different clusters within the phasor distribution correspond to bright lipid droplet-associated granules within hESCs (red), the hESCs themselves (green) and the MEF feeders (blue). Transmission image (a) and two-photon fluorescence intensity image (c) of a undifferentiated hESC colony grown on MEF feeders. (d) Phasor color map. Pixels of different colors correspond to the color of the cluster in the phasor plot A. Arrow indicates a MEF. (e) Expression of the pluripotency marker OCT4 in the same colony of B after cell fixation and immunostaining. (f) DAPI staining. (g) Merge of dapi and OCT4 staining. Arrow indicates a MEF, whose nucleus does not express OCT4.

Figure 14:
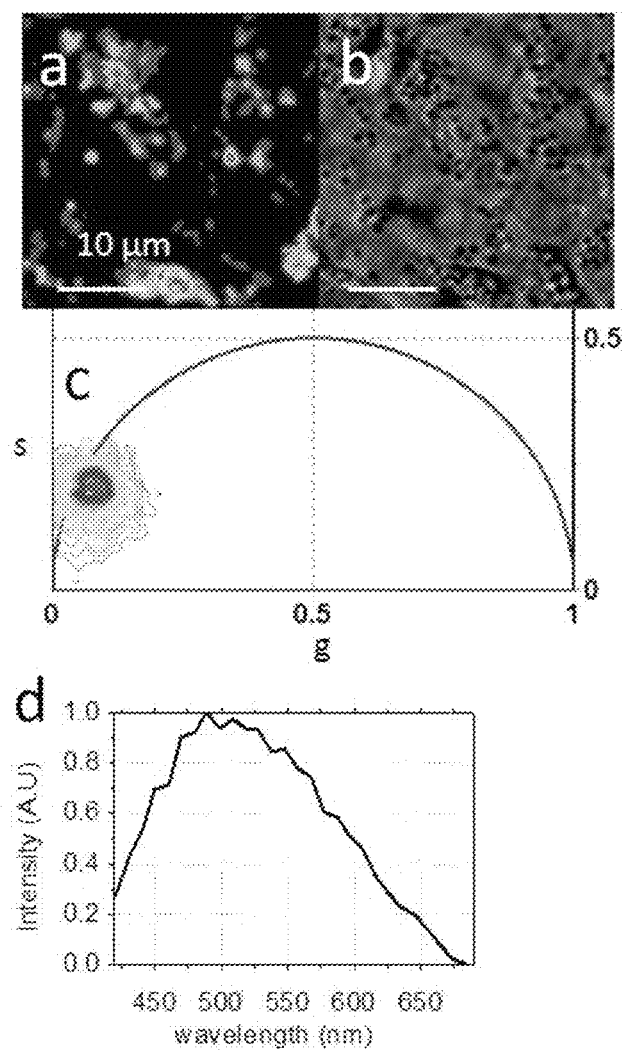

FIG. 14 Spectroscopic characteristics of granules in hESCs. Two-photon fluorescence intensity image (a) and transmission image (b) of a single undifferentiated H9 hESCs colony. (c) FLIM phasor plot of the FLIM image excited at 760 nm of the hESCs colony area in (a). (d) Emission spectrum from hESCs granules in (a).

Figure 15:
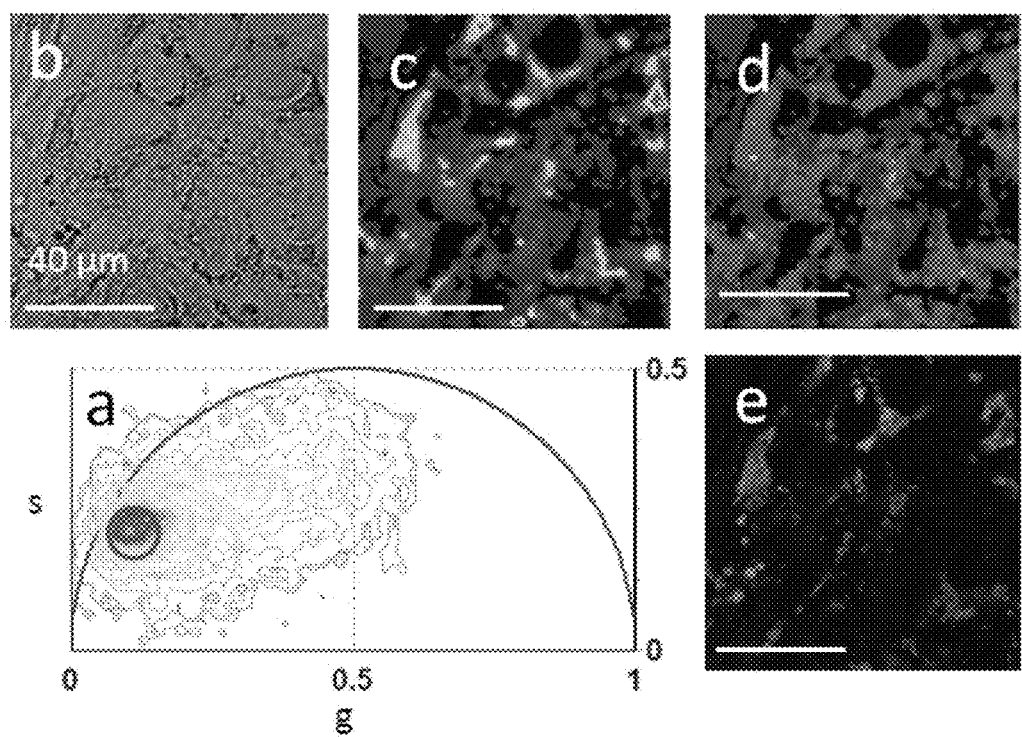

FIG. 15 Colocalization of Lipid droplets with granules in hESCs. (a) FLIM phasor plot of the FLIM image excited at 760 nm of a single undifferentiated H9 hESC colony area. The red cluster in the phasor plot specifically selects some bright granules within the hESCs. Transmission image (b) and two-photon fluorescence intensity image (c) of the hESCs colony area. (d) Phasor color map. Red pixels have a specific lifetime signature that is selected by the red cluster in the phasor plot A. (e) in vivo staining of lipid droplets with Bodipy 493/503 shows colocalization with the hESCs granules identified by FLIM in D and A.

Figure 16:
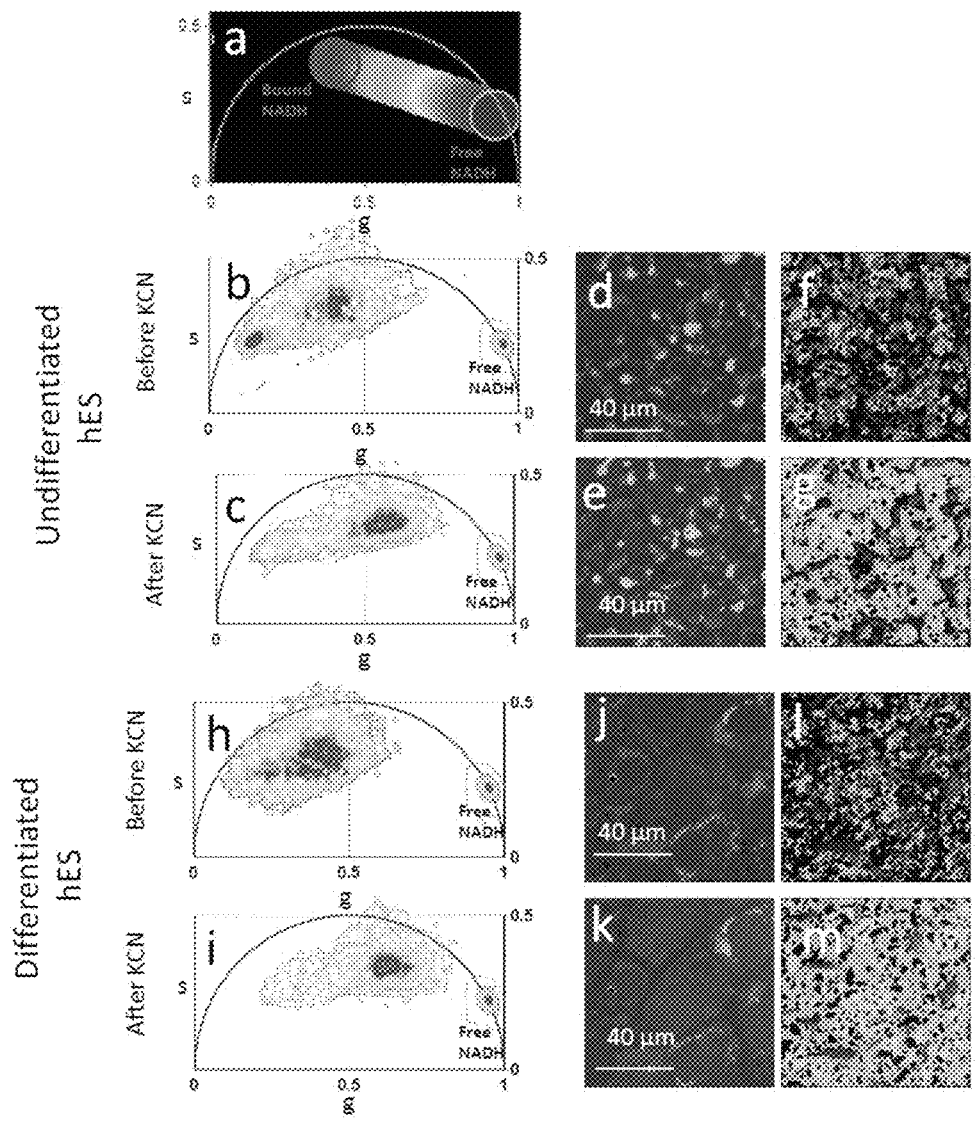

FIG. 16 shows the effect of electron transport chain inhibition on the hESC FLIM phasor distribution.

(a) Phasor plot selection using linear cluster combination that represents all the possible relative concentrations of Bound NADH and Free NADH. The phasor locations of pure bound and free NADH have been measured in ref Stringari et al 2011. Each point along the line has a color corresponding to specific relative concentration of free/bound NADH. Red color indicates a high free/bound NADH ratio, while orange, yellow, green, cyan and blue indicate linearly and progressively decreasing ratios free/bound NADH ratio. In vivo FLIM phasor plot of an undifferentiated H9 hESC colony (b,c) and a differentiating H9 hESC colony (h,i) before and after the treatment with potassium cyanide (KCN). Two-photon fluorescence intensity images of the undifferentiated hESC colony (d-e) and differentiating hESC colony (j-k) before and after the KCN treatment. Phasor color map images representing the relative concentrations of bound and free NADH in the undifferentiated hESC colony (f-g) and the differentiating hESC colony (l-m) before and after the KCN treatment. By blocking the respiratory chain in hESCs, the FLIM phasor distribution shifts toward the location of the free reduced NADH (c, i) and the cell concentration of free NADH increases with respect to bound NADH (g,m).

Figure 17:
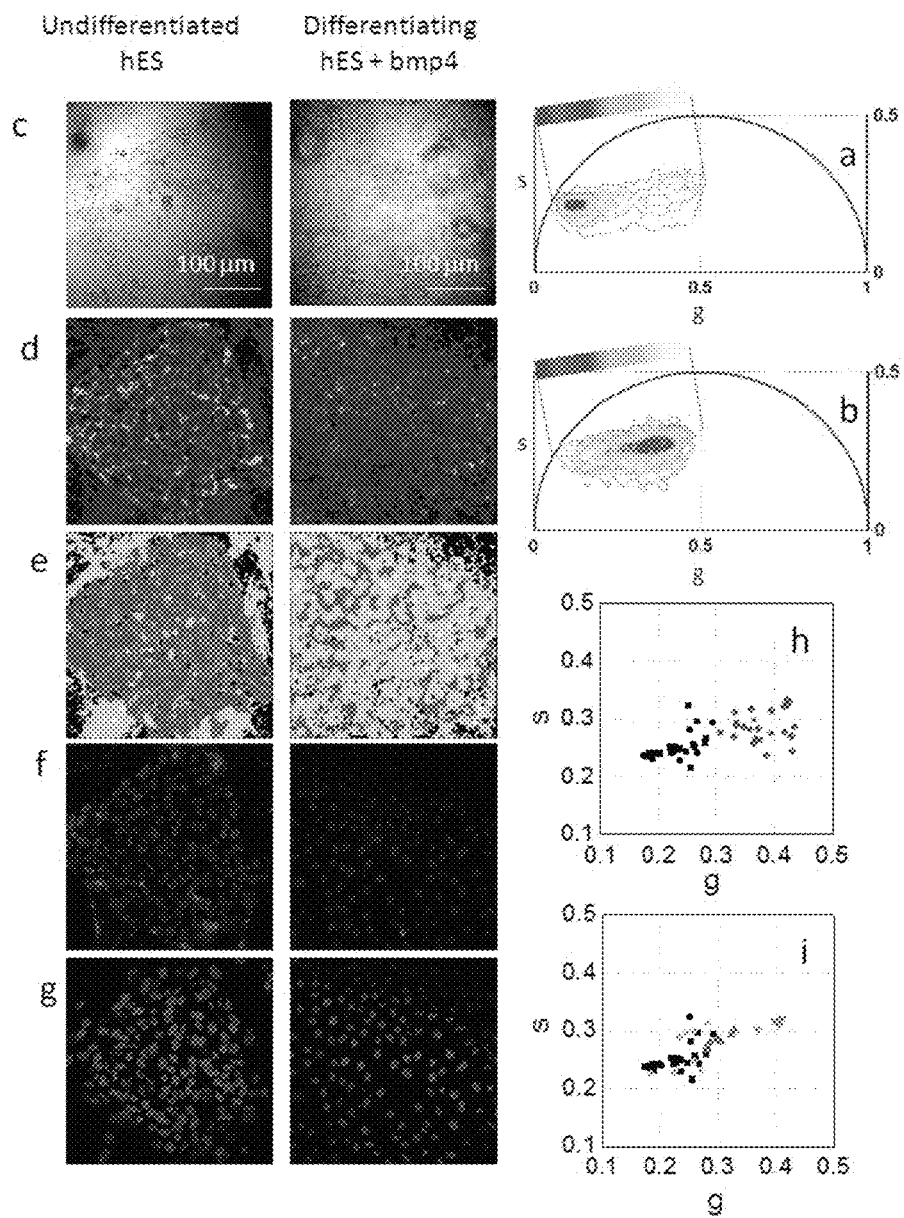

FIG. 17 shows FLIM Phasor separates undifferentiated from differentiated hESC colonies.

FLIM phasor plot of the FLIM image excited at 760 nm of a single undifferentiated H9 hESC colony area (a) and a differentiating H9 hESC colony treated BMP4 medium for four days (b). Phasor plot selection using linear cluster combination that represents all the possible relative contributions of the hESCs granule FLIM signature (purple) identified in FIG. 1 and FIG. 2 and the NADH FLIM signature typical of the MEFs (cyan-white), identified in FIG. 1 and FIG. 3. Each point along the line has a color that corresponds to a specific relative concentration of the two species. Transmission images (c) and two-photon fluorescence intensity images (d) of the undifferentiated hESC colony and the differentiating hESC colony. (e) Phasor color map images representing the relative concentration hESC granules (purple) and NADH (cyan-white) according to the color scale in fig A and B (f) Expression of the pluripotency marker OCT4 (g) DAPI staining. (h-i) Scatter plot of the phasor FLIM signature of hESC colonies. Every point represents the average phasor value of an entire hESC colony. Black and cyan squares represent undifferentiated H9 colonies (N=27) and undifferentiated H1 colonies respectively (N=8). Red circle represent differentiating H9 colonies treated BMP4 media for four days (N=24), purple triangle H9 hESC colonies differentiating in a medium without bFGF (N=6), orange triangles H9 hESCs induced to differentiate in RA medium for four days (N=6).

Figure 18:
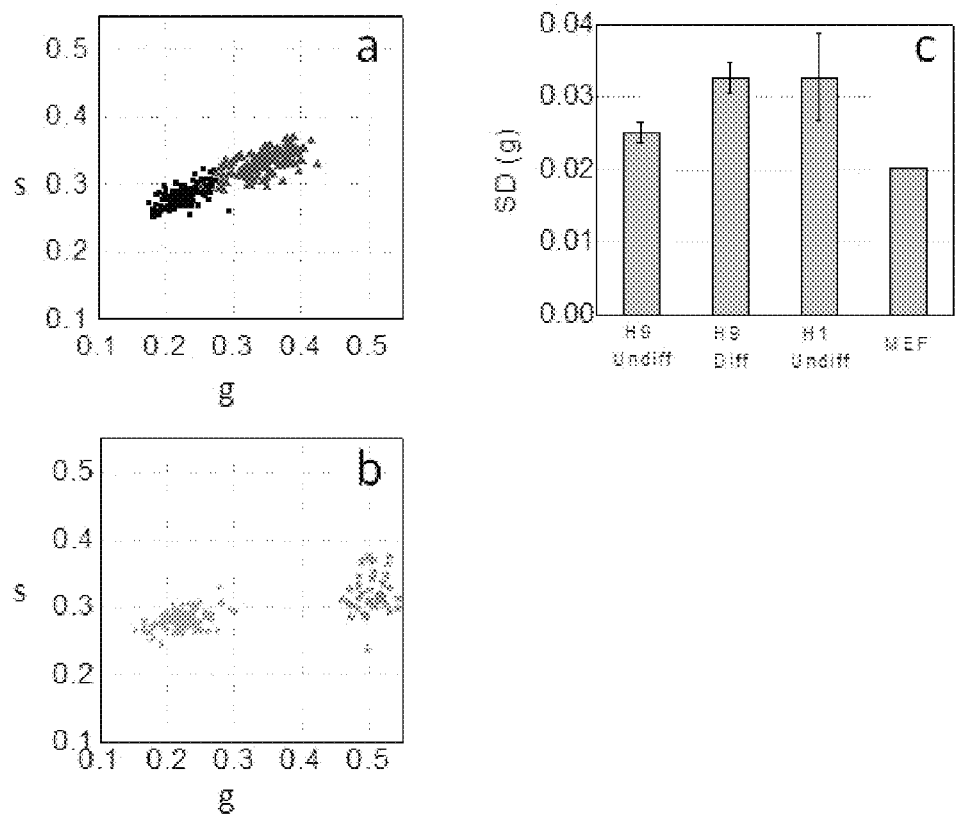

FIG. 18 Heterogeneity within hESC colonies:

(a) Scatter plot of the phasor FLIM signature of individual hESCs from the two colonies displayed in FIG. 5. Every point represents the average phasor value of a single hES cell. Black squares represent undifferentiated H9 hESCs (Ncells=123) and red triangles represent differentiating H9 hESCs treated with BMB4 media for four days (Ncells=136) (b) Cyan circles represent the cell phasor of H1 hESCs (Ncells=119) from the colony and green stars represent MEFs (Ncells=42). (c) Standard deviations (Ncolony=3) of the phasor g coordinates of the cell phasor of single hESCs from an undifferentiated H9 colony, differentiating H9 and H1 colony and MEFs.

Figure 19:
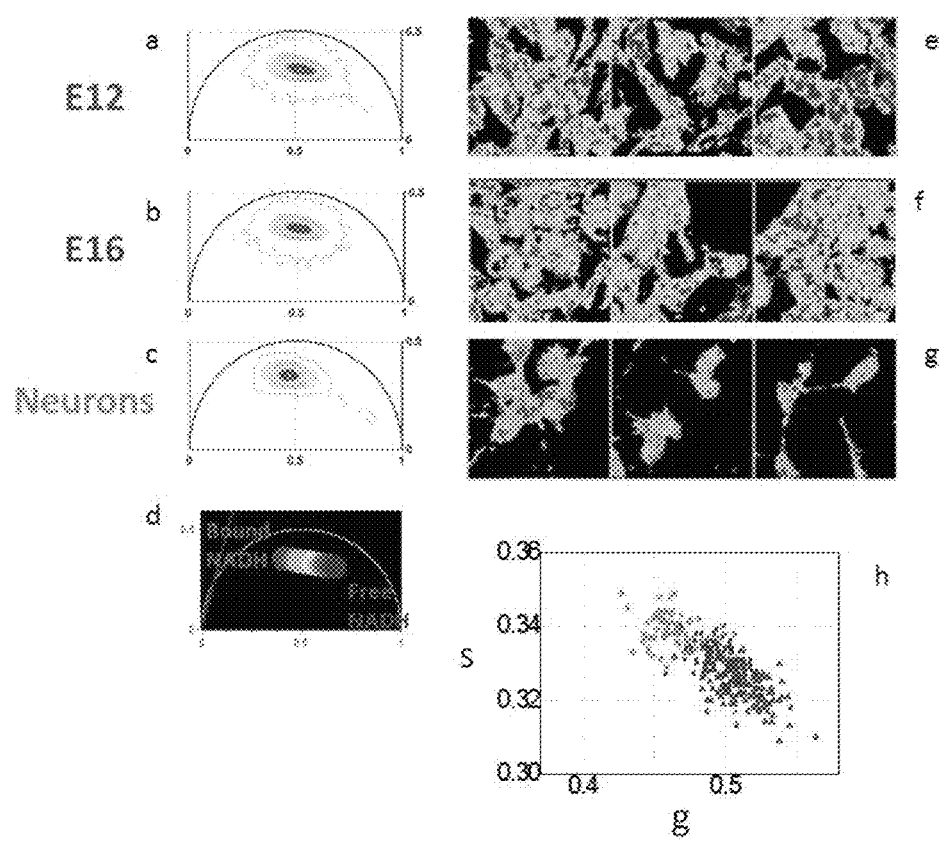

FIG. 19 shows Phasor FLIM distinguishes between Neuronal stem/progenitor cells (NSPCs) from different developmental ages that are committed to different differentiation fates. (a-c) FLIM phasor plots of the FLIM image excited at 740 nm of NSPCs from earlier (E12) (a) and later (E16) (b) developmental time points and from differentiated neurons (c). (d) Phasor plot selection using linear cluster that represent all possible relative concentrations of Free NADH (red) and bound NADH (blue). Red color indicates a high free/bound NADH ratio, while orange, yellow, green, cyan and blue indicate linearly and progressively decreasing ratios free/bound NADH ratio. (e-g) Phasor color maps of relative concentrations of free NADH (red) and bound NADH (blue) of E12 (e), E16 (f) and neurons (g). (h) Scatter plot of the mean values of the phasor signature of NSPCs E12 (red triangles), E16t (blue squares) and neurons (green stars). The three populations are statistically different.

Figure 20:
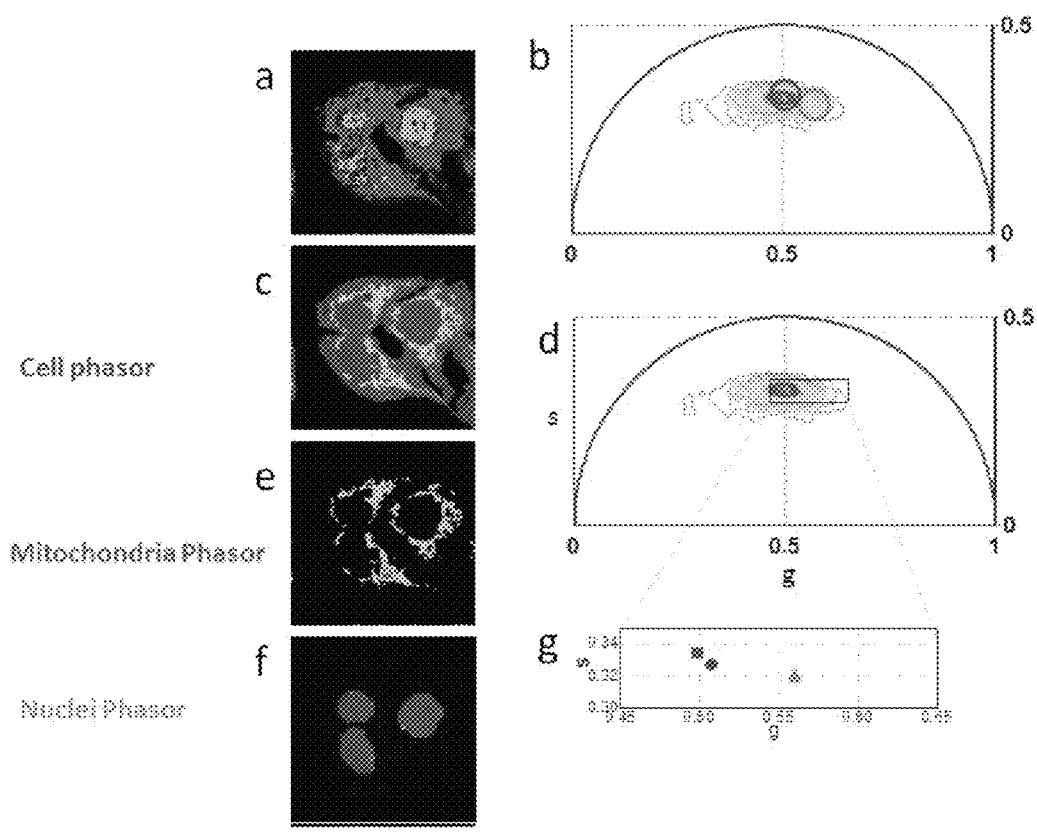

FIG. 20 shows that Phasor FLIM sense subcellular metabolism:

(a) Phasor color maps of the FLIM image of three cancer cells. The colors of pixels correspond to the clusters of cell components identified in the phasor plot b; green selects the nucleus, while red selects the mitochondria and the rest of the cell cytoplasm. (b) FLIM phasor histogram of the FLIM image excited at 740 nm from three colon cancer cells. Different clusters within the phasor distribution correspond to the cell nuclei (green) and the mitochondria and the rest of the cell cytoplasm (red) (c) Intensity image of the autofluorescence excited at 740 nm from three colon cancer cells. (d) same FLIM phasor plot in b (e) the mitochondria in the cells are selected by intensity threshold (f) the nuclei of the cells are selected by image segmentation using a cursor of arbitrary shape. (g) zoomed area of the Phasor plot in d. Average phasor values of cellular compartments are represented by a red square (average phasor of mitochondria), blue circle (average phasor of the entire cell) and the green triangle (average phasor of).

Figure 21:
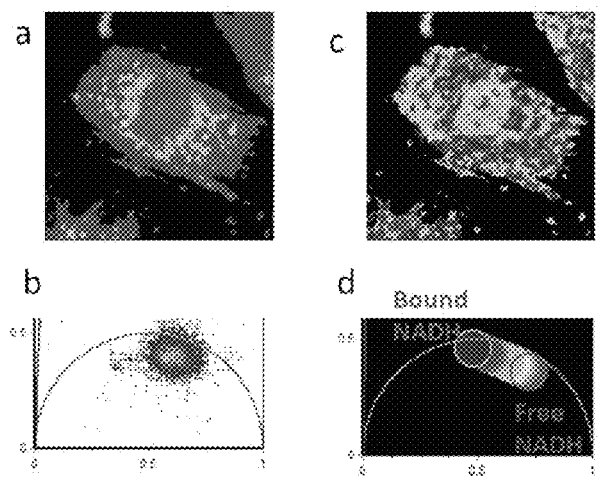

FIG. 21 shows NADN/NAD+ heterogeneity in the nucleus of an undifferentiated myoblast cell:

(a) Intensity image of the autofluorescence excited at 740 nm from an undifferentiated myoblast cell. (b) FLIM phasor histogram of the FLIM image of the undifferentiated myoblast cell excited at 740 nm (c). (c) Phasor color map images representing the relative concentration of bound NADH (blue) and free NADH (yellow-orange) in the cell. Within the nucleus there are island of higher values of bound/free NADH, i.e. of NAD+/NADH ratios. (d) Phasor plot selection using linear cluster combination that represents all the possible relative contributions of free NADH (red-orange) and bound NADH (blue).

Figure 22:
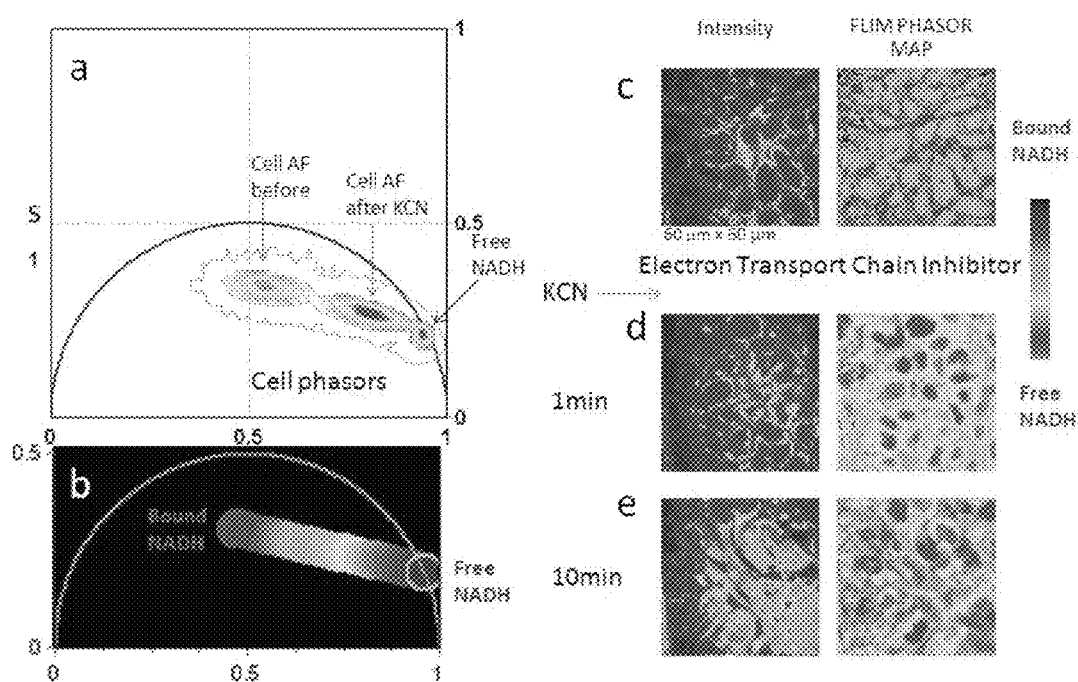

FIG. 22 show the sensitivity of Phasor approach in detecting intracellular metabolic changes upon drug application, such as Potassium Cyanide (KCN):

(a) FLIM phasor histogram of the FLIM image of human colon cancer cells excited at 740 nm before and after the application of KCN. (b) Phasor plot selection using linear cluster combination that represents all the possible relative contributions of free NADH (red-orange) and bound NADH (blue) (c-e) Fluorescence intensity images and Phasor color map images representing the relative concentration of bound NADH (blue) and free NADH (yellow-orange) in the cell for cells before the application of KCN (c), after 1 minute (d) and 10 minutes (e) after the addition of the KCN drug.

DETAILED DESCRIPTION OF THE INVENTION

Figure 3:
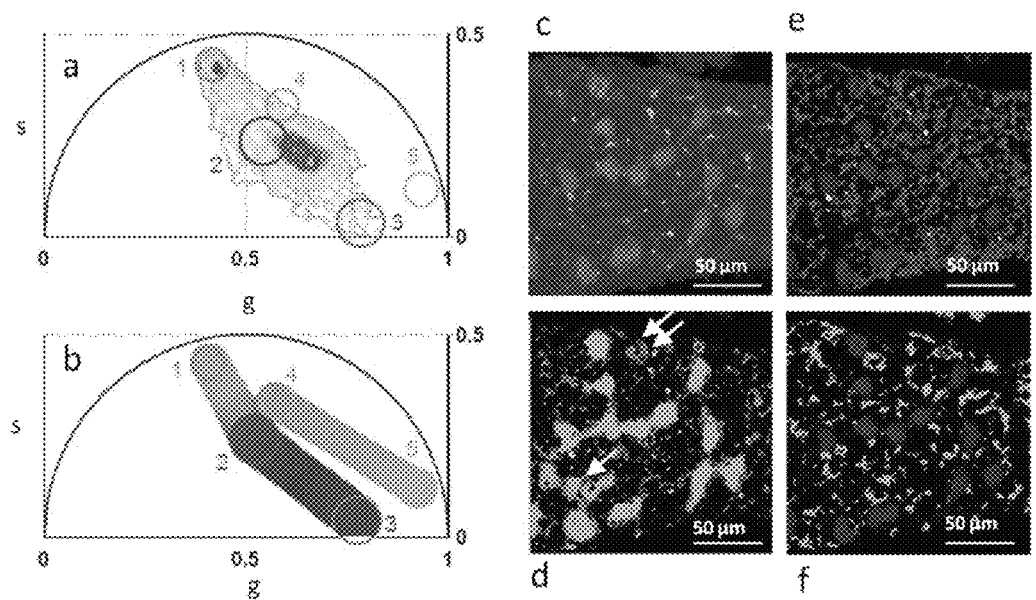
FIG. 3 Shows maps of relative concentration of tissue components. (a) Phasor plot of the FLIM image. Different clusters are assigned to pure chemical species according to FIG. 2a: GFP (1), average tissue auto fluorescence (2), collagen (3), retinol (4) and retinoic acid (5). (b) Phasor plot selection using linear cluster that represent all the possible relative concentrations of GFP and the average autofluorescence, of autofluorescence and collagen, and retinol and retinoic acid, respectively. Each point along the line has a color corresponding to specific fractional intensity of the species. (c) Intensity image of a semininiferous tubule from a mice expressing green fluorescent protein (GFP) from an Oct4 transgene (d-f) Maps of the relative concentrations of: GFP and auto-fluorescence (d), auto fluorescence and collagen (e) for retinol and retinoic acid (f). Pixels in the images are highlighted with the same color scale of the phasor plot.
Figure 4:
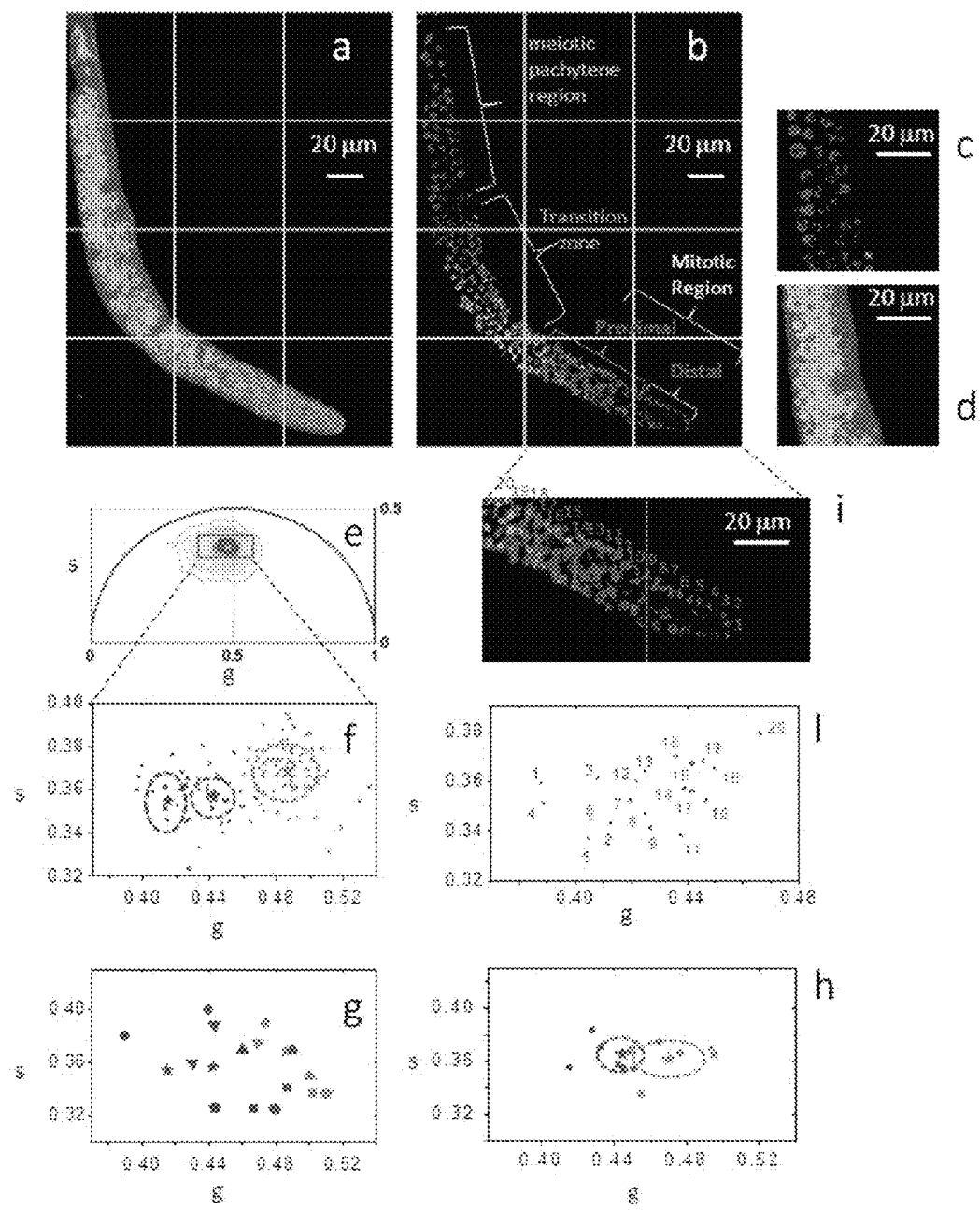
FIG. 4 shows the identification of metabolic states of germ cells during differentiation.

As a preliminary matter, it should be noted that numerous modifications we made in the phasor method and the analysis software as disclosed herein, with respect to the 2008 phasor method published (reference 36). Such modifications, include, but are not limited to:

a) modification of the phasor method to perform image segmentation to measure the average phasor value of regions of interest in the tissues. The region of interest of cells is selected by using a circular of custom diameter or an arbitrary shape Different regions of the image, such as cells, can be attributed statistically to different average phasor values. (FIG. 4).

b) modification of the phasor method to measure the relative concentrations of fluorophores and map their spatial distribution in living tissues. (FIG. 3 and FIG. SM2).

c) modification of the phasor method to perform analysis of the FLIM data with higher harmonics ($\omega=n\omega_o$ with n=2, 3) of the laser repetition rate ($\omega_o=2\pi f$), where f is the laser repetition rate, i.e. 80 MHz. (See supplementary Material in the Manuscript). The multi-harmonic analysis can separate several tissue components that have the same phasor location, but have a different lifetime distribution. (FIGS. SM4 and SM5).

Results

Phasor Cluster Analysis Separates Individual Tissue Components

The phasor transformation of FLIM images (described in the Supplemental material) of a living tissue directly provides maps of individual tissue components without a priory assumption on the number of species in the tissues (Jameson 1984; Clayton 2004; Redford 2005; Colyer 2008). The analysis of the FLIM data in the phasor space is performed by detecting clusters of pixel values in specific regions of the phasor plot. FIG. 1a displays 2-photon excited fluorescence image of seminiferous tubules from mice expressing EGFP from an Oct4 transgene. The FLIM image is presented in FIG. 1b in term of the average lifetime $\tau\phi$ (Material and Methods). The lifetime is relatively homogeneous across the image and the histogram of lifetime values (grey distribution in FIG. 1c) has a range from 0 ns to 2 ns with two major peaks at 0.8 ns and 1.8 ns. We perform the phasor analysis of the FLIM image by a mathematical transformation of the raw data (see Material and Methods). FIG. 1d displays the two-dimensional phasor plot of the FLIM image. Every pixel of the FLIM image is transformed into a pixel in the phasor plot. All the pixels are located inside the universal circle of the phasor plot, thus indicating that their decay is multi-exponential. The phasor distribution of the living tissue has a complex shape with different clusters. Their positions specifically correspond to different tissue components. In FIG. 1e pixels are highlighted with a color that corresponds to the clusters in the phasor plot in FIG. 1f. Based on morphology, the green-colored cluster selects cells, the blue cluster fibers in the basal membrane, the red cluster the rest of the tissue and the grey one selects specific bright granules.

Identifying Tissue Components Using the Phasor Plot

Each chemical species has a specific location in the phasor plot that is determined by the intrinsic characteristics of its fluorescence decay. This characteristic phasor fingerprint is used here to identify individual components in a complex system such as a tissue. FIG. 2a shows the phasor location of the most important intrinsic fluorophores. Their positions in the phasor plot are well defined and clearly separated one from the other. The majority of fluorophores have decay with multiple exponential components because of their conformational heterogeneity. The phasor position of pure GFP is near but not exactly on the universal circle (FIG. 2a) since the fluorescence decay of GFP is not single exponential (Hess 2003). Collagen has a very short lifetime with a broad distribution of decay components due to the intermolecular cross links (Bornstein 1966). Its phasor is located inside the universal circle and closed to the temporal zero. The phasor position of retinol in DMSO has a specific location which is different from the one of the retinoic acid in DMSO, in agreement with the measured multi-exponential decays in ref (Bel'Kov 1990). Both FAD and free and bound NADH phasor position are located inside the phasor plot. Their lifetime is a combination of several exponential (Lakowicz 1992; König 2003; Schneckenburger 2004; Chia 2008). NADH has a different phasor position when binds with different enzymes such as lactate Malate dehydrogenase (MDH) and lactate deyhidrogenase (LDH) (Lakowicz 1992). The phasor position of protoporphyryn IX (in dimethylformamide and methanol) is located on the universal circle since it is characterized by a single lifetime component (Brancaleon 2004).

The phasor position can be obtained from published lifetime decay data after application of the phasor transformation. We emphasize that in the phasor approach it is the location in the phasor plot that characterizes a specific tissue component.

Figure 2:
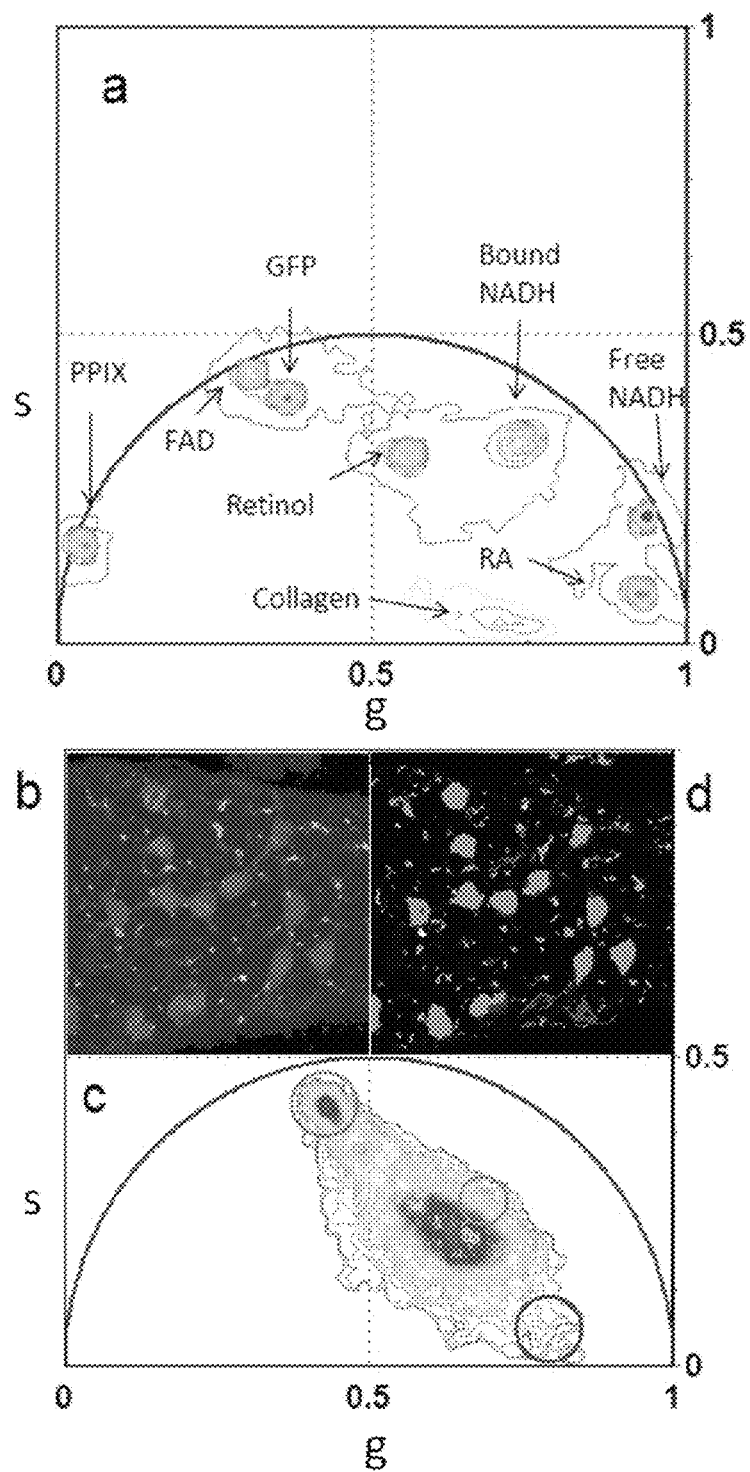
FIG. 2. Shows phasors of pure chemical species identify tissue components. (a) Phasor location of pure chemical species. GFP in Tris buffer, Retinol in DMSO (pH 8.5), Retinoic acid in DMSO (pH 8.5), FAD in water (pH 7.4), free NADH in Mops buffer (pH 7), bound NADH in Mops buffer (pH 7) and lactate dehydrogenase, Protoporphyrin IX in dimethylformamide:methanol (pH 7). (b) Intensity image of a semininiferous tubule from a mice expressing green fluorescent protein (GFP) from an Oct4 transgene. A chain of spermatogonial stem cells lie on the surface of the seminiferous tubule. (c) Phasor plot of the FLIM image acquired in b. The green and the blue cluster are located in the phasor position of pure GFP and pure collagen clusters. (d). Phasor color map. Pixels of different colors correspond to the color of the cluster in the phasor plot. Green and blue pixels contain mostly GFP and collagen.

The phasor location of the molecular species in FIG. 2a is used as a reference to analyze the phasor distribution in FIG. 2b that is acquired from seminiferous tubules from a testis of an Oct-4-GFP mouse. The blue and the green clusters in FIG. 2b are located in the position of the phasor that correspond to the pure GFP and pure collagen measured in FIG. 2a. In the phasor color map in FIG. 2.d the blue and green pixels represent all the points in the tissue in which GFP and collagen are in the focal volume with very small contribution of other fluorescence components. High fractional intensities of GFP with respect to the auto-fluorescence is located in the germ cells that form a chain on the surface of the tubule. The presence of collagen in the tissue is also confirmed by second harmonic generation (SHG) microscopy (Campagnola 2003). The SHG signal that is detected in the tissue (FIG. SM1) co-localizes with the blue selected collagen pixels in FIG. 2b Mapping the Relative Concentrations of Tissue Components in a Seminiferous Tubule.

FLIM measurement is independent from the absolute concentration of a fluorescent species but reveals the relative concentration of two or more fluorophores weighted by their intensity. In the phasor plot a combination of two chemical species lie on the line connecting the two phasors (see Material and Methods). The phasor position of the bright granules areas that are identified by the orange cluster in the phasor plot 2.b do not co-localize with any of the pure chemical species of FIG. 2.a. However we identify them as a mixture of retinol and retinoic acid since their position in the phasor plot is located along the straight line between the retinol and the retinoic phasor position. Retinoids are located in Sertoli cells of the seminiferous tubule and regulates germ cell fate and their transition to meiosis (Bowles 2006; Lin 2008). The presence of retinol and retinoic acid was confirmed by spectral imaging (Supplementary FIG. SM3). The average auto-fluorescence arising from the tissue locates in the central part of the phasor plot (red phasor cluster in FIG. 1.a) because it is a mixture of different intrinsic fluorescent components such as FAD and retinoids.

We provide a map of the relative concentration of individual components within the tissues by visualizing their fractional intensities to the signal (FIG. 3). Within the same phasor plot the phasor locations of five different molecular species are selected by different clusters based on the chemical species fingerprint in FIG. 2a. In FIGS. 3a and 3b the colored clusters are assigned respectively to GFP (green), the average tissue auto fluorescence (red), collagen (blue), retinol (orange) and retinoic acid (cyan). We calculate firstly the relative concentration of GFP with respect to the average auto fluorescence, then the average auto fluorescence with respect to the collagen and lastly the retinol concentration with respect to the retinoic acid. The relative concentration is calculated in every pixel of the image with a graphical analysis, by the position of the pixel in the phasor plot along the line connecting the two molecular species. In FIG. 3b a linear cluster with a color scale from green to red shows all the possible relative concentrations of GFP and average auto fluorescence. Each point along the cluster has a color corresponding to specific fractional intensities. The same color scale is used to map the relative concentration of the two species in FIG. 3d. The phasor position of cells with different expression of GFP lie along the line between the GFP position and the auto-fluorescence phasor points.

Using this principle, we directly visualize different state of differentiation of the germ within the tissue. In FIG. d the last three stem cells of the chain contains a smaller ratio of GFP to auto fluorescence with respect to the other cells of the chain they are differentiating thus decreasing the expression of Oct-4GFP. The relative concentration of auto fluorescence and collagen is calculated and mapped in FIG. 3e with a color scale from red to blue while that of retinol and retinoic acid is shown in FIG. 3f with a color scale from orange to cyan.

In Vivo Identification of Changes in Metabolic State as Germ Cells Differentiate Excitation of intrinsic fluorescent species can be avoided or maximized by tuning the excitation wavelength of the Ti:sapphire laser. Collagen, GFP and FAD two-photon excitation cross section have a peak around 900 nm while NADH is maximal around 740 nm (Huang 2002; Zipfel 2003). FIG. 4 shows the fluorescence intensity images acquired in the living tissue from C. elegans germ line excited at 740 nm (FIG. 4a) and at 880 nm (FIG. 4b and FIG. 4e). The germ line expresses a histone-GFP fusion protein that allows identifying the differentiation state of the germ cells. The distal pool of the mitotic region (FIG. 4e) contains undifferentiated cells maintained in a "stem cell-like state", while the proximal pool cells that are maturing toward early differentiation. The transition zone contains early differentiated (crescent cells), while the meiotic pachytene region contains differentiated germ cells (Cinquin 2010).

FIG. 4e shows the phasor distribution of the FLIM image excited at 740 nm. The intrinsic fluorescence of the tissue is a mixture of FAD and NADH, which are both excited at 740 nm. We confirm the presence of these metabolites by spectral imaging (FIG. SM2).

We perform image segmentation by selecting the regions of interest of germ cells with a circular cursor of 5 μm diameter (red cursor in FIGS. 4c and 4d). The average phasor value of a germ cell is calculated within the circular cursor. We plot the average phasor values of germ cells in the scatter diagram of FIG. 4f.

Cell phasor fingerprints cluster according to their differentiation state (mean values of cell clusters are indicated by the stars and standard deviation by the dotted lines). The distribution of cells of the mitotic distal pool (blue), the mitotic proximal pool (red), the distal crescent cells (green) and the crescent cells (purple) are significantly different (t-test, $p<0.05$ FIG. 4f), while the distributions of crescent cells (purple) and pachytene cells (cyan) are not separated (t-test, $p=0.14$ FIG. 4f) and their distributions overlap. The same trend has been found in N=5 samples of *C. Elegans* germline. The phasor fingerprints of the stem cells as they differentiate shows heterogeneity in the concentration of FAD and free and bound NADH. During differentiation the concentration of FAD decreases while the concentration of bound NADH increases with respect to free NADH (FIGS. SM2 a and b). The blue shift in the spectrum during differentiation (FIGS. SM2 c and d) is in agreement with an increase of the bound/free NADH ratio during differentiation. FIG. 4h shows the phasor fingerprint of cells in the mitotic region according to their position from the distal tip (FIG. 4g). We assume that the distal mitotic region (blue cells in FIGS. 4g and 4h) has a uniform state of "stemness" (Cinquin 2010). This allows us to identify two different metabolic states of cells when the difference between their phasor values is greater than the standard deviation of the distal mitotic region cluster (blue circle in FIG. 4h). The trend in the phasor fingerprints of cells of the mitotic region (FIGS. 4g and 4h) suggests a gradient in the expression of regulators promoting differentiation and self renewal, which influence the metabolic states of cells.

Label Free Identification of Stem Cells in the Small Intestine:

Our method provides a label-free identification of stem cells in a living tissue of small intestine. Freshly excised tissues are imaged with two photon microscopy and FLIM within two hours. Lgr5-GFP mice are used to mark the Lgr5+ stem cell population at the base of small intestine (SI) and colon crypts.

We observe that different compartments of the tissue are defined by unique Phasor FLIM signatures. We can distinguish collagen fibers (orange red in FIG. 11d) at the base of the crypts, the lamina propria and the vascular network (blue in FIGS. 10d and 11g), and the epithelium (cyan-white in FIG. 10d and FIG. 11g).The green area sin FIG. 10c shows the location of stem cells that are expressing GFP at the base of the small intestine crypt. We use a cursor (gray line in FIG. 10 (a-d)) with an arbitrary shape to select the stem cell.

The FLIM signature at the base of the crypt at 740 nm (FIG. 10d) follows exactly the map of stem cells intercalated between adjacent Paneth cells. Paneth cells (purple) are characterized by a different FLIM signature with respect to the stem cells thus indicating a difference in the concentration and/or composition of intrinsic fluorophores.

Three Dimensional Phasor FLIM Reveals Different Metabolic States of Epithelia Stem Cells During Differentiation in a Small Intestine and Colon Crypts.

Here we perform label-free Phasor Fluorescence lifetime microscopy (FLIM) to reconstruct the three dimensional metabolic signature of small intestine and colon tissue in vivo.

The FLIM Z-stack reveals a shift of the metabolic signature of crypt epithelial cells during differentiation. Stem cells at the base of the crypt have the shortest lifetime (cyan FIG. 11.g) and the highest NADH/NAD+ ratio. Movement up the crypt to transit amplifying cells and fully differentiated cells on the mucosal surface corresponds to different FLIM signatures that correspond to decreasing NADH/NAD+ ratios (white FIG. 11.g), as is expected during differentiation. FIG. 11k shows the metabolic fingerprint of epithelial stem cells change with the Z-depth in the small intestine crypts, i.e. with the state of cell differentiation.

Temporal Phasor FLIM Imaging Reveals the Role of Wnt Signaling in Colon Cancer Cell Metabolism.

Wnt signaling is misregulated and overactive in the majority of colon cancers and is necessary to drive cancer cell proliferation, primarily through regulation of the cell cycle (Miyoshi 1992; He 1998; Tetsu 1999; van de Wetering 2002). Sustained proliferation in cancer cells also correlates with an altered metabolic profile. This shift in metabolism has been characterized as the Warburg effect, or a shift in metabolism from oxidative phosphorylation to aerobic glycolysis (Warburg 1956). Our study addresses the hypothesis that in addition to cell cycle control, Wnt signaling also contributes to the cancer cell phenotype through regulation of cancer cell metabolism. In order to address this hypothesis, we created stable clonal colon cancer cell lines that inducibly express dominant negative LEF-1 (dnLEF-1) in order to block activation of a sub-set of Wnt target genes. Cell cycle analysis of this cell line reveals no change upon dnLEF-1 expression, and levels of c-myc and p21 are also unaltered. Therefore any changes observed from dnLEF-1 expression are independent of changes in the cell cycle or c-myc expression. Microarray analysis reveals that a large subset of dnLEF-1-regulated genes are metabolically linked.

FIG. 12 shows the mapping of the free/bound NADH in the cancer cells and their Phasor FLIM metabolic fingerprints over time. At day 4 there is a decrease in free/bound NADH levels with dnLEF-1 expression (FIGS. 12c,d,g). This trend is consistent with a decrease in the ratio of glycolysis to oxidative phosphorylation. Consistent with this trend, several genes downregulated by dnLEF-1 play important roles in the metabolic shift toward aerobic glycolysis. Overall this data suggests that Wnt signaling plays an important role in maintaining a Warburg-type metabolic profile in colon cancer cells.

Identification of the Intrinsic Biomarkers in Human Embryonic Stem Cell Colonies We separate and identify different intrinsic fluorescent metabolites in the hESC colonies by detecting clusters with different FLIM signatures within the phasor plot. After label free FLIM imaging we perform retrospective in vivo staining or immunostaining after fixation to colocalize the FLIM signature of intrinsic fluorescent biomarkers with specific hESC compartments.

Figure 1:
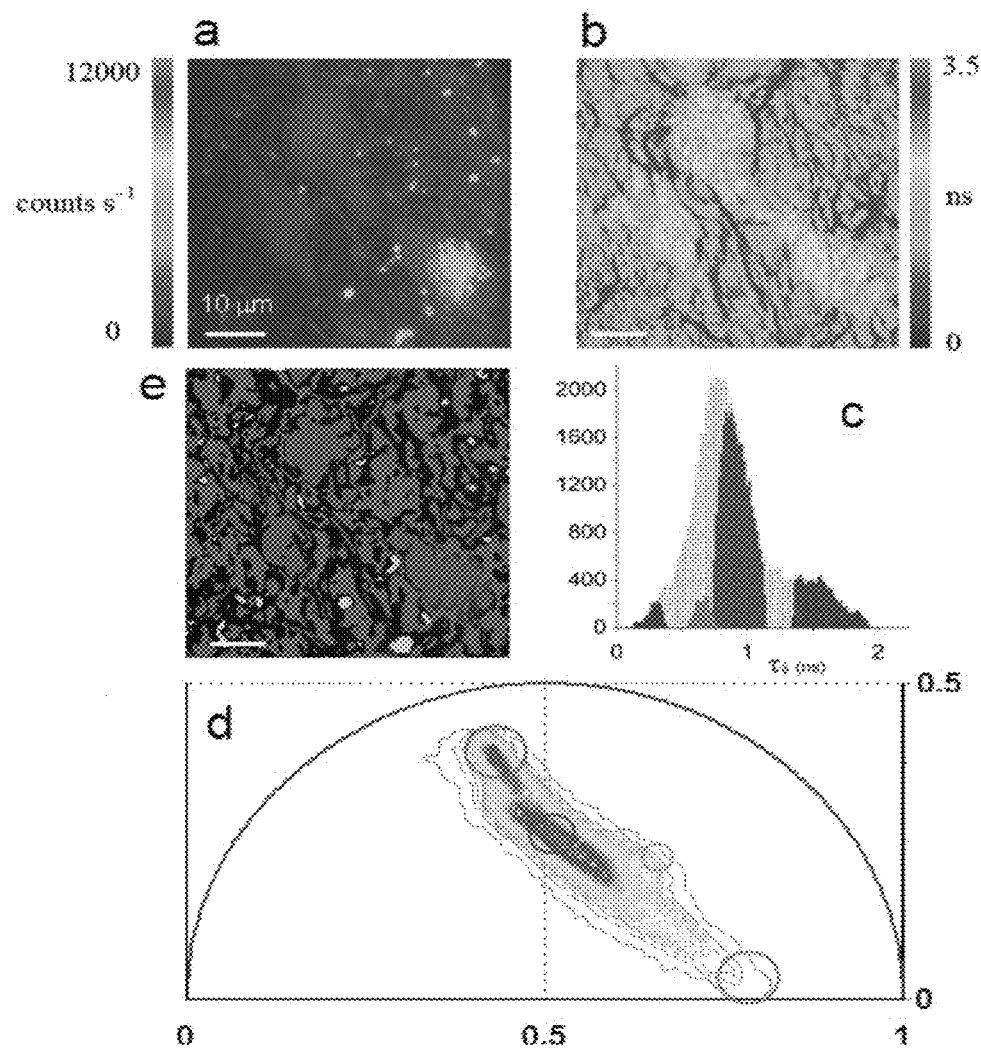
FIG. 1. Shows a phasor analysis of FLIM tissue images. (a) Intensity image of a semininiferous tubule from a mice expressing green fluorescent protein (GFP) from an Oct4 transgene. (b) Map of the average lifetime $\tau\varphi$ of the FLIM image. (c) $\tau\varphi$ histograms of the FLIM image is represented in grey. The colored areas correspond to the $\tau\varphi$ of each tissue component identified by the phasor analysis. (two components "red" and "green" are shown here) (d) Phasor plot of the FLIM image. Four clusters corresponding to different tissue components are identified in the phasor distribution with different colors. (e) Phasor color maps of the FLIM image. The colors of pixels correspond to the clusters of tissue components identified in the phasor plot.

FIG. 1 shows a representative image of the autofluorescence from a colony of undifferentiated H9 hESCs plated on a mouse embryonic fibroblast (MEF) feeder substrate. We perform the phasor transformation of the FLIM image of the hESC colony (see Material and Methods and ref (Stringari 2011)). Every pixel of the FLIM image is transformed into a pixel in the phasor plot. FIG. 13a displays the phasor histogram distribution of the FLIM image of an undifferentiated hESC colony that is located inside the universal circle of the phasor plot, indicating the multi-exponential characteristic of its decay (Stringari 2011). Within the phasor distribution we can identify three main clusters that correspond to different cell types and cell compartments (FIGS. 13a and 13d). hESC nucleus and cytoplasm, bright granules within the hESCs and the MEFs are selected by the green, red and blue cluster respectively (FIGS. 13a and 13d). After label-free FLIM imaging, we fixed the cells and we performed retrospective immunostaining imaging (see material and methods) for the phenotypic identification of undifferentiated hESCs and MEFs. Undifferentiated hESCs are identified by the expression of the pluripotency transcription factor OCT4 (FIG. 13e-g), while MEFs are identified by dapi staining and the absence of OCT4 expression (arrows in FIG. 1f-g).

The specific bright granules within the hESCs are identified by the red cluster in FIG. 13a and are homogeneous in dimensions and typically have a diameter of ~1 μm. (FIGS. 14a and b). They are characterized by a long lifetime distribution (FIG. 13a-d and FIG. 14c) very close to the universal circle (defined in Supplementary material) and the single exponential of about 10 ns. Although the hESCs granules have a very similar lifetime to protoporphyrin IX (Stringari 2011) we exclude its presence because the hESCs granules emission spectrum (FIG. 14d) is very different with respect to protoporphyrin IX spectrum that has a peak at 630 nm (Smits 2005). In fact the emission spectrum of the hESC granules is very broad and it has a peak at 500 nm (FIG. 14d). FIG. 15 shows the colocalization of hESC granules with lipid droplets (LDs) labeled in vivo with 4,4-difluoro-1,3,5,7,8-pentamethyl-4-bora-3a,4a-diaza-s-indacene (BO-DIPY493/503). These Lipid Droplet-Associated Granules (LDAGs) might contain fluorescent oxidized low density lipoproteins (oxLDLs) and Lipid peroxidation-modified proteins that are biologically active (Freubis 1992; Riazy 2011). Linoleic acid and arachidonic acid peroxides can form fluorescent products from the interaction with polypeptides and free amino acid groups of proteins (Freubis 1992; Riazy 2011). Lipid peroxidation occurs when polyunsaturated fatty acids interact with ROS, which are a byproduct of oxidative phosphorylation. Hence the formation of LDAGs in hESC can be generated by the combination of high ROS level, associated to high oxidative phosphorylation rate (Birket 2011) and the abundance of unsaturated metabolic precursor, such as arachinoid acid, that are highly reactive under oxidative conditions (Yanes 2010).

These LDAGs might also be aggregates of proteins and enzymes that are in excess in hESCs (Cermelli 2006; Ohsaki 2006). LDs serve as storage depots of protein and are involved in various cellular activities and in intracellular protein metabolism during development (Cermelli 2006). Recent studies show that LDs contain enzymes involved in lipid metabolism, signaling molecules and proteins related to membrane trafficking, PAT family proteins, enzymes involved in the eicosanoid formation, enzymes for cholesterol synthesis, signaling proteins, caveolin, Rab proteins and histones (Ozeki 2005; Cermelli 2006; Ohsaki 2006). To identify the contribution of NADH to the autofluorescence detected in the center of the Phasor plot, we treat the hESCs with potassium cyanide (KCN) to block oxidative phosphorylation during cellular respiration and increase the levels of the reduced form of NADH. When hESCs are treated with KCN the FLIM Phasor distribution shifts toward the location of the free reduced NADH (FIGS. 16 C and I of Supplementary Material) and the concentration of free NADH increases with respect to bound NADH (FIGS. 16 G and M of Supplementary Material).

Average Phasor FLIM Discriminates Undifferentiated hESCs from Differentiating hESCs Colonies We measured the metabolic signature of hESC differentiation by monitoring the concentrations of the intrinsic fluorescent biomarkers NADH and LDAGs. In FIG. 17 we identified the differences between the FLIM phasor signature of undifferentiated hESCs and differentiating hESCs. To induce differentiation, we cultured hESCs in the presence of BMP4 or Retinoic acid while simultaneously removing basic fibroblast growth factor (bFGF) from the culture media, which is critical to the maintenance of hESC pluripotency and self-renewal (See material and methods).

The FLIM phasor distribution of undifferentiated hESCs (FIG. 17a) is dominated by the contribution of the hESC granules identified in FIG. 13-14-15. On the other hand, the FLIM phasor distribution of differentiated hESCs treated with BMP4 (FIG. 17b) is shifted towards the central region of the phasor plot represented by the FLIM fingerprint of NADH ((Stringari 2011), FIG. 16). We used a phasor linear cursor (colored bar in FIG. 17a-b) to represent all possible contributions of the LDAGs (purple) and the NADH (cyan-white). Every single color along the line represents a different relative concentration of the two fluorescent metabolic markers. The colored FLIM map of FIG. 17e shows that the H9 undifferentiated hESC colony has a higher concentration of LDAGs with respect to NADH, while the differentiating hESC colony has a much lower concentration of LDAGs with respect to NADH.

In FIGS. 17h and 17i we measured the Phasor FLIM signature of the entire hESC colony by calculating the average value of its phasor FLIM distribution (see material and methods). FIG. 17i shows that the FLIM signatures of undifferentiated hESCs from two different cell lines, H9 (black squares) and H1 (cyan circles) are localized in the same region of the phasor plot and are not statistically different (t-test p3.34). The Phasor FLIM signatures of undifferentiated H9 hESCs (black squares in FIG. 17h) are statistically different (t-test $p<0.0001$) from differentiating H9 hESCs treated with either BMP4 (−bFGF) medium (red circles in FIG. 17h), RA (−bFGF) medium (orange triangles in FIG. 17i) or −bFGF only medium (purple triangles in FIG. 17i). While the hESCs treated with RA and BMP4 are not statistically distinguishable (t-test p=0.25), colonies cultured in the absence of bFGF are statistically different from both conditions (t test $p<0.0001$) and have a Phasor FLIM signature closer to that of undifferentiated hESCs (FIG. 17i).

The trend in FIGS. 17h and 17i of the Phasor FLIM signatures of the H9 colonies during differentiation reflects differences in relative concentration of LDAGs and NADH, that is mapped in FIG. 17e. The increase of NADH concentration during early hESC differentiation is in agreement with the decrease of oxidative phosphorylation rate with respect to glycolysis during early hESC differentiation (Birket 2011). The high number of LDAGs in undifferentiated hESCs might reflect the need to reserve excess proteins in lipid droplets for later transportation and release in designated areas within the cell.

We believe that the abundance of LDAGs in undifferentiated hESCs indicates the accumulation of fluorescent lipid peroxidation-modified proteins generated by the interaction of ROS and unsaturated lipids. Hence the decrease in LDAGs concentration during differentiation can reflect a decrease in ROS level following a decrease in oxidative phosphorylation rate (Birket 2011), a decrease in the abundance of unsaturated eicosanoids, such as Linoleic acid and arachidonic acid, that promote pluripotency (Yanes 2010), the activation of oxidation and a decrease in antioxidant enzymes concentration (Cho 2006; Hamanaka 2010).

Cell Phasor FLIM of Heterogeneity in hESCs

The Phasor FLIM analysis at single cell resolution reveals heterogeneity in the metabolic signature and intrinsic biomarker content of hESCs within the same colony. We exploit the Cell phasor Phasor concept and image segmentation (Ref (Stringari 2011) and material and methods) to measure the phasor FLIM signature of single hESCs by calculating the average value of the phasor Phasor distribution of single hESCs. (See material and Methods)

FIGS. 18a and 18b shows the plot of single hESCs from an undifferentiated H9 colony (black dots), an undifferentiated H1 colony (cyan dots) and a differentiating H9 colony treated with BMP4 (red dots). The cell phasor cluster of undifferentiated H9 hESCs is smaller in size compared to the cell phasor cluster from differentiating H9 hESCs (FIG. 18a) and the standard deviation of the g component (defined in supplementary material) of the cell phasors from and undifferentiated H9 colony is smaller than the one of differentiating H9 hESCs (FIG. 18c). This observation indicates that the FLIM signature of single hESCs in a H9 colony becomes more heterogeneous during differentiation. Cell Phasor and FLIM signature of single hESCs is determined by the relative concentration of the intrinsic fluorescent metabolites NADH and LDAGs (FIG. 14, FIG. 15 and FIG. 16). The cell phasor reveals the metabolic signature of the cells that might be associated with the stem cells phenotype and be indicative of commitments to different differentiation pathways. The higher degree of cell phasor heterogeneity within the H1 hESC colonies (FIG. 18c) might reflect the higher phenotypic heterogeneity and differential expression of hESC markers that are known to be present in H1 hESC-lines (Allegrucci 2007).

Moreover, FIG. 18c shows that the cell phasor cluster size of both undifferentiated and differentiating hESC colonies are smaller than the size of the MEF cluster (green dots in FIG. 18b). The heterogeneity in the FLIM/metabolic signatures of hESCs might reflect different cell phenotypes and plasticity that are reduced in a defined fully differentiated cell types such as MEFs.

Average Phasor FLIM Metabolic Fingerprint of Neuronal Stem Cells from Different Developmental Ages Predicts their Fate Early cortical Neuronal stem/progenitor cells (NSPCs) generate primarily neurons, whereas later in development they give rise predominantly to glia (Walsh 1992; Grove 1993; Levison 1993; Luskin 1993; Qian 1998; Qian 2000).

FIG. 19 shows that Phasor FLIM has the capability to discriminate different metabolic states of stem cells associated with neuronal differentiation. Neuronal stem/progenitor cells have a different metabolic map (FIGS. 19a,b,e,f) with respect to differentiated neurons (FIGS. 19c,g) and their metabolic Phasor fingerprint is statistically different (FIG. 19h).

We measure different Phasor FLIM signatures (FIG. 19.h) and free/bound NADH maps (FIG. 19.e,f) in NSPCs from earlier, E12 and later, E16 developmental time points. Stem cells that are committed to a neuronal fate have an higher free/bound NADH ratio with respect to the stem cells that are committed to a glial fate. We demonstrate that by measuring the metabolic activity and redox ratio of cells by Phasor Fluorescence Lifetime Microscopy is possible to predict the commitment of stem cells to different differentiation pathways, independent of the expression of lineage marker expression profiles.

Sensing Cellular and Sub Cellular Metabolism with Phasor FLIM

The average Phasor is very sensitive to small differences of free/bound NADH ratio and senses small subcellular differences in metabolites. The average phasor of different cell compartments reveals a different concentration of free/bound NADH (FIG. 20) in the cell nuclei and mitochondria. Cell average Phasor, Nuclei average Phasor and mitochondria average Phasor are located in separated areas of the Phasor plot (FIG. 20.e). FIG. 20.e shows that cell nuclei have a higher ratio of free/bound NADH with respect to the mitochondria and the cytoplasm.

Mapping the relative concentration of free and bound NADH ratio (FIG. 21) allows visualizing the NADH/NAD+ ratio in the nucleus. FIG. 21 shows that within the nucleus the NADH/NAD+ ratio is not homogeneous and there are regions with higher NADH/NAD+ ratios, that are localized is specific areas of the chromatin. Histone post-transcriptional modifications and epigenetic mechanisms are known to sense the variation of metabolites levels NADH/NAD+. (Zhang 2002; Fjeld 2003; Sahar 2009). Phasor FLIM would allow to map transcription territories via mapping the NADH/NAD+ ratio.

FIG. 22 shows how Phasor FLIM can detect and map the cellular metabolic response to a drug. When Potassium Cyanide (KCN) is added to the cells, the phasor distribution of the intrinsic autofluorescence shifts toward the position of the Free NADH. (FIG. 22.a) and the free NADH progressively accumulates in the cells (FIG. 22.c, d,e) over the time.

Discussion

The term "a tissue sample" as used herein refers to any material obtained from an animal or human, including individual cells or tissue sections.

The term "living tissue" as used herein refers to any extracted solid living tissue or cells which is part of a living mammalian individual, such as a human being or mouse. Such tissues/cells can be observed using the disclosed method in physiological conditions. Tissues can be excised from animals within 2-3 hours from the animal death. In vivo, i.e. uncultured, (or fresh tissues) measurements provide information on the cellular activity and metabolic states of stem/cancer cells.

In other embodiments, fixed tissues or cells can also be analyzed using the disclosed method.

The term "a fluorescence lifetime imaging microscope apparatus" refers to any microscope that is capable of performing fluorescence lifetime imaging as well as any ancillary components connected with the microscope use to generate or enhance the fluorescence signal or detect the fluorescence signal. This may also include the slides/chambers holding one tissue/cell sample or a chamber holding an array of these samples.

The term "image segmentation" as used herein refers to the process of partitioning an image into multiple regions of interest based on homogeneous characteristics, morphology or intensity. The term "metabolic state of cells" as used herein refers to a condition of chemical reactions which occurs in living organisms to sustain life.

The term "average phasor value" as used herein refers to the average value of the distribution of pixels in the phasor plot that belong to a region of interest of the image The term "phasor location" as used herein refers to a specific position of a pixel or average phasor value such a cell phasor or region of interest phasor plotted within the phasor plot.

The term "lifetime distribution" as used herein refers to the ensemble of the single exponential and multi-exponential components that constitute the complex fluorescence lifetime decay of one fluorophore, cell, region of interest or image.

The term "phasor plot" as used herein refers to a two-dimensional histogram graph with two axes where the x-coordinate is the "g" component referring to the cosine transform of the intensity decay and the y-coordinate is the "s" component which is the cosine transform of the intensity decay in the time domain.

The term "a computer program product" as used herein refers to media (such but not limited to a CD-Rom) or electronic tool (such as but not limited to a memory stick) that can hold a computer program and which can be inserted into a computer. It can also mean the computer program itself if the program is transferred or downloaded from another computer or via the internet (local or world wide web); or a program that is stored and utilized by others one a shared server or "cloud".

The term "cell phasor" as used herein refers to the "average phasor value" calculated in one cell The term the "region of interest phasor" as used herein refers to the "average phasor value" of a region of interest Here we show that the phasor approach to FLIM can map stem cell metabolism in label-free living tissues. This method provides a metabolic fingerprint of cells and can identify and classify stem cells and differentiating cells according to their metabolic state. We measure small metabolic changes during differentiation and map metabolic gradients in tissues.

Phasor approach is a "fit-free" method that requires no assumption or a priori knowledge on the biological system, such as its biochemical content. We separate and identify tissue components by cluster analysis, i.e., detecting clusters of pixel values in specific regions in the phasor plot (FIG. 1). This method provides high selectivity in identifying fluorescence components that cannot be separated by a multi-exponential fitting or by analyzing the average lifetime, as for example auto-fluorescence or collagen. Multi-exponential fitting can separate only a limited number of components in a mixture of multiple fluorescence species. The mean lifetime offers a contrast whose physical interpretation is ambiguous and cannot separate tissue components with the same average lifetime but characterized by different lifetime distributions (FIG. SM3). The phasor approach instead provides excellent discrimination of intrinsic molecular sources in live tissues, where the majority of pixels have a complex multi-exponential decay. (FIG. 1, FIG. SM4 and FIG. SM5).

We determine the phasor location of some relevant endogenous fluorophores, i.e. collagen, free and bound NADH, FAD, retinol, retinoic acid and porphyrin. However the number of fluorescent chemical species that can be identified by their phasor signature is not limited. The phasor location of every molecular species in the histogram is uniquely determined by their fluorescence decay. The phasor fingerprint of chemical species reduces the importance of knowing the exact lifetime distribution of fluorophores decay and allows interpreting FLIM images directly in terms of chemical species. The phasor location of endogenous fluorophores is used as a guide to identify them in mice and in *C. Elegans* germ lines (FIG. 2, FIG. 3 and FIG. SM2). Phasors allow an easy quantification of the relative concentration of molecular species in living tissues. Phasor coordinates are a linear function of molecular species and mixture of fluorescent species are identified by a graphical analysis. We measure and map the relative concentration of fluorescent species (FIG. 3 and FIG. SM2) directly from the position of the pixel in the phasor plot on the straight line connecting the two chemical species.

We calculate the average phasor values of stem cells in the tissue by a image segmentation of the FLIM image (FIG. 4). Germ cells at different differentiation level in the *C. Elegans* are statistically attributed to different average phasor values and we can separate them by their metabolic state (FIG. 4*f* and FIG. 4*h*). The evolution of the stem cell phasor fingerprint during differentiation (FIG. 4*f*) reflects a decrease in the concentration of FAD and an increase in the ratio of bound/free NADH (FIG. SM2), in agreement with the literature (Guo 2008; Uchugonova 2008; König 2010). Growth factors that promote self-renewal cause stem cell to become more reduced, while signaling molecules that promote differentiation cause progenitor to become more oxidized (Smith 2000). The change in the metabolic fingerprint during differentiation (FIG. 4*e*) may also suggest a change in the binding sites of NADH with different coenzymes such MDH and LDH (FIG. 2 and FIG. SM2). The gradient of cell phasor fingerprints in the mitotic region (FIG. 4*h*) reflects a progression from undifferentiated stem cells to early differentiation. This may also reflect a contribution of the distal dip cell to the signal. Phasor fingerprint heterogeneity among mitotic cells (FIG. 4*h*) could reveal symmetric and asymmetric divisions occurring at the level of the niche. In fact its signaling controls the production of stem cells daughter and differentiated progenies at the level of individual cells.

FLIM has previously been used to distinguish different states of stem cells in vitro (Guo 2008; Uchugonova 2008; König 2010). However the phasor approach to FLIM provides a quantitative and straightforward interpretation of physiological processes in living tissues. This method simultaneously identifies a large number of molecular components in a tissue, allows fast analysis of large data sets and provides a global overview of the decay properties by analyzing all pixels of the image at the same time. Moreover the phasor approach to FLIM provides metabolic fingerprints of cells and tissues without any fitting procedure and assumption. Hence it allows an identification and classification of metabolic states of cells in a similar way of flow cytometry scattergrams. With this approach it is possible to easily discriminate undifferentiated stem cells from different stages of differentiation (FIG. 4) and possibly identify asymmetric divisions. Time lapse phasor FLIM imaging can be performed to obtain information on the dynamics of cell activity, physiological processes thus monitoring tissue development over time. The phasor method to FLIM is capable to measure small differences in metabolic states among stem cell (FIG. 4*h*). Relatively small changes in intracellular metabolites levels over a narrow range can modulate cell fate and function with profound difference in outcome (Smith 2000; Lonergan 2006; Parker 2009). Hence the cell phasor fingerprints of cells could be used to predict stem cell fate and to characterize stem cells plasticity and their commitment to differentiation. It would be also interesting to monitor the metabolic fingerprint evolution in the phasor plot of different differentiation pathways to cell lineages.

The phasor approach in tissues is a promising tool in biology, biophotonics and biomedical research to track in vivo metabolic changes that are associated with stem cell differentiation, cell carcinogenesis and apoptosis. It could provide important insight into the signaling pathways and regulatory networks, which are involved in cell self-renewal differentiation and oncogenesis in a variety of tissue and organs. The phasor approach to FLIM would also be helpful to monitor cell metabolism and at the same time characterize the three-dimensional microenvironment of tissues by detecting extracellular matrix remodeling and molecular gradients. The ability to observe and isolate noninvasively cancer cells and stem cells based on their metabolic rate in living tissues has important implications for early diagnosis and new therapeutic strategies. The detection of malignant transformation of progenitor cells, aberrant differentiation of cancer cells could be performed in vivo. Label-free discrimination between self-renewal and differentiation by phasor approach to FLIM would be suitable to non-invasively monitor embryonic stem cells and to design new approaches to reprogram somatic cells to a pluripotent stem cell fate. The phasor approach to FLIM could be of interests to label-free cell sorting and high throughput screening for drug discovery, cell replacement therapies and tissue engineering.

In one embodiment, we disclose a method for to discriminate the in vivo metabolic state of cells in a tissue comprising performing fluorescence lifetime imaging microscopy to said tissue sample to generate a fluorescence lifetime imaging data of said tissue; and performing image segmentation to measure the average phasor value of regions of interest in the tissues, whereby the relative concentration of the tissue components are determined. The average phasor value provides a very sensitive way of interpreting the FLIM data with scatter plots, similar to fluorescence-activated cell sorting (FACS). The Phasor analysis is fit-free and provides an unbiased representation and interpretation on the raw FLIM data. Thus, a method is disclosed which does not introduce any fitting procedure and any mathematical model, namely, a method that doesn't make any a priori assumption on the system. This method measures relative concentration of fluorophores with a sensitivity that are unmatched with other methods/procedures. The method can distinguish different cells that have a different distribution and concentration of intrinsic metabolic biomarkers. We can recognize cells with different redox states and metabolic states.

This method is very sensitive and has the capability to detect biological noise. It is a fit-free (non-fitting) method. Not all cells are equal and the average phasor can measure the stochastic noise and processes in biology. Cells are different and this method can measure and identify their metabolic states. We never expected to have this sensitivity that arises from applying the image segmentation to the phasor analysis of FLIM data (phasor average concept). Nobody has achieved this sensitivity in detecting metabolites concentration and metabolic cell states.

Other people have used image segmentation methods (Pelet 2004) for FLIM, but never in conjunction with a fit-free FLIM analysis. There are other "non-fitting" techniques (Jo 2004; Dabir 2009) for FLIM that are clearly different from the Phasor approach to FLIM. All the "non-fitting" techniques and "fitting" techniques with multi-exponentials (Lee 2001; Siegel J 2003; Becker 2004; Pelet 2004; Munro 2005; Chorvat 2009; Fu 2009) in FLIM never achieved our sensitivity in measuring relative concentrations and cell states.

The phasor method as disclosed is especially powerful with respect to the classical multi-exponential fitting, when resolving many fluorophores or tissue components with multiple exponential lifetimes (FIG. 7) because it does not require the assignment of the exponentials to the molecular species.

Further, the method disclosed allows us to achieve a high sensitivity to distinguish cell states because we introduced the concept of average phasor in combination with image segmentation: when we calculate the average phasor of a cell or region of interest (ROI), all pixel of the cell/ROI (about 1000) are taken in account. The signal to noise ratio of the FLIM signature of cells is higher than in single pixels. This increased signal to noise ratio allows us to distinguish small differences of redox ratio and see gradients of metabolites concentration. (FIG. 4*l*).

The differences in the S and G coordinates (in FIG. 4I) of average cells phasors with different metabolic states are in the order of modulus of |phasor 1-phasor 2|=0.01 or 1%.

The signal to noise ratio of the cell average phasor is higher than the signal to noise ratio of the pixel phasor, depending on the number of pixels that we average and on the number of photons/counts in every pixel. If for example the cell is constituted by 100 pixels and if all pixels have the same number of photons, the signal to noise ratio of the cell average phasor is increased by a factor 10 with respect to the signal to noise ratio of the pixel phasor. (i.e. if the pixel S/N ratio is 1 the cell phasor (100 pixels) S/N ratio in 10)

This increased signal to noise ratio allows us to distinguish between small differences of redox ratio and see gradients of metabolites concentration. (FIG. 4*l*). More over when we measure the phasor average of the cell multiple times in the same condition we find that its average phasor is always in the same position. Variation in the average phasor position would therefore indicate a real variation of the metabolic concentration, i.e. a change in the metabolic state of the cell. Accordingly, the disclosed method can distinguish phasors positions that differ by about 1% which means that cells with slightly different metabolic states can be distinguished. Since the term "position" cannot be applied to the conventional method, we cannot comment about the "consistency" of position of the conventional methods available.

The multi-exponential fitting method requires assumption on the model and initial conditions on the parameters. For this reason the final fitted parameter are not robustly and univocally determined, but depend on the model you chose and the initial conditions.

In one embodiment, a possible sequence of the methodology for any typical experiment is as follows. However, it should be noted that various combinations of these steps, and different sequences of the steps (and others not mentioned) are envisaged. Accordingly, the scope of the claims should not be limited to the following sequence of steps:

i) Cell culture/tissue is excised from the animal and imaged within 2 hour/live animal is prepared for imaging ii) We perform a FLIM measurement either in the time domain or in the frequency domain iii) We transform the FLIM data in the Phasor representation with mathematical transformations iv) We perform a cluster analysis of the phasor distribution and we identify different tissue components v) We use a reference data base of the phasor fingerprint of pure molecular species vi) We map the relative concentration of tissue components or metabolites in the cells/tissue.

vii) We perform image segmentation, by selecting cells or subcellular compartments with a cursor of an arbitrary shape viii) We calculate the average phasor of every cell or region of interest.

ix) We represent the average phasors in a scatter plot and we perform statistical analysis In one embodiment, it a computer program or computer program product comprises the above sequence of the methodology; or any combinations of the sequences thereof.

Using the Method to Purify Cells to be Used for Further Studies or Transplantation This method allows identifying the metabolic states of cells either in culture or in living tissues. Once the cells are identified with a statistical analysis based on their metabolic states and intrinsic biomarker concentration, they can be extracted and isolated from the cell culture or tissues with mechanical methods that use physical pressure or a suction force. Once the cells have been isolated and sorted they can be grown as a pure population, tested and then used for clinical transplantation. After transplantation, cells can be measured in the transplanted tissue to determine if they are proliferating or not.

One of the hallmarks of carcinogenesis is a shift from cellular oxidative phosphorylation to cellular glycolysis for ATP production. Neoplastic cells have an increased metabolic demand relative to normal cells because of rapid cell division, and neoplastic metabolism is associated with changes in the relative concentrations of bound to free NADH. Moreover many enzymes bind to NADH in the cancer metabolic pathway.

Cancer detection is usually performed at the macroscopic level with magnetic resonance imaging MRI or positron emission tomography (PET).

Our method represents a label-free optical technique that can obtain molecular measurement with high resolutions at the level of single cell and sub-cellular level. Label-free is important because is the only way cells can be imaged in humans in a non invasive way It provides information on the complexity, diversity and in vivo behavior of cancers molecular oncology and of intracellular signaling pathway. Our method allows to measure biological stochastic noise at the level of single cells and detect anomalous variation in the intrinsic metabolic biomarkers concentration that are related to early stages of cancer mutation.

Our method provides quantitative read-outs (statistical analysis of the average phasor scattergrams) that are longitudinal (label-free and non invasive monitoring over time), standardized, and very sensitive to molecular perturbations.

Automated Phasor FLIM analysis can have several applications for high throughput screening, metabolomics analysis, small molecules testing and drug screening. Cells can be isolated based on their metabolic states and then tested. The metabolic response of single cells can be measured in a label-free, fast, straightforward and sensitive way. Small molecules, metabolic compounds and drugs can be easily tested with our method. This allows developing new therapeutic strategies for different diseases and new strategies for tissue engineering.

Resolvability:

The disclosed method has high powers of resolvability i.e. it can resolve and distinguish many tissue component (see FIG. 7), regardless the complexity of the decay—see also multiharmonic analysis (FIG. 8 and FIG. 9)).

The phasor as disclosed identifies the molecular species by using their phasor fingerprints, without resolving and assigning exponential components to the fluorescence species. This method provides high selectivity in identifying fluorescence components that cannot be separated by a multi-exponential fitting or by analyzing the average lifetime. Multi-exponential fitting can separate only a limited number of single exponential components (maximum 2-3 component), i.e. a few components (maximum 2-3) in a mixture of multiple fluorescence species.

The mean lifetime offers a contrast whose physical interpretation is ambiguous and cannot separate tissue components with the same mean lifetime but characterized by different lifetime distributions (FIG. 7a). The phasor approach and the multi-harmonics phasor analysis instead provide excellent discrimination of intrinsic molecular sources in live tissues, where the majority of pixels have a complex multi-exponential decay (FIG. 1, FIG. 7b, FIG. 8 and FIG. 9).

FIG. 2a shows that our method as disclosed can distinguish 8 intrinsic fluorophores within the phasor plot at the same time: (GFP, FAD, collagen, retinol, reticoic acid, free NADH, NADH bound to and lactate dehydrogenase, Protoporphyrin IX).

There is no limit in the number of tissue components or fluorophores that can be distinguished in the phasor plot using the disclosed method.

—Robustness:

The method as disclosed is robust in terms of analysis (Fit-free, is a representation of FLIM raw data, unbiased representation, no a-priori assumption is required, average phasor data are represented with scatter plot, similar to fluorescence-activated cell sorting (FACS). The phasor method as disclosed performs only a mathematical transformation (see formulas in the supplementary material) on the FLIM intensity decay. The phased is a graphical representation of the raw FLIM data. In contrast, conventional multi-exponential fitting methods do not use scatter-plots.

Speed:

The method as disclosed can be performed relatively fast because it does not require any fitting/modeling, but only a mathematical transformation. Consequently, it is less time consuming with respect to the multi exponential fitting; all pixel of the images are analyzed at the same time, many images (up to 26 images) are analyzed at the same time. Moreover, the phasor transformation is instantaneous, because it is a mathematical transformation. On the other hand the conventional/classical multi-exponential fitting requires much more time to fit one or two single exponential components in every pixel of the image or on the entire image with a global fit.

The shortest time that has been published to perform a global fit one entire FLIM image of 256 pixel×256 pixels with two-components and the deconvolution of the lamp is 500s (Pelet 2004).

Summary of Some of the Novel Observations Obtained from Using the Disclosed Method:

1) Intrinsic fluorophores, (collagen, retinol, retinoic acid, porphyrin, flavins, free and bound nicotinamide adenine dinucleotide (NADH)) have been identified and separated in different living tissues, such as seminiferous tubule from a mice testis, *C. Elegans* germline, small intestine 2) Gradients of Retinol and Retinoic acid have been detected in a seminiferous tubule of a mice testis.

3) A trend in metabolite (free and bound NADH and FAD) concentrations in the germ cells along the main axis of the *C. Elegans* germ line is measured. During germ cell differentiation the concentration of FAD has been found to decrease, while the concentration of bound NADH has been found to increases with respect to free NADH 4) Colon cancer cells were found to have a higher redox ratio (NADN/NAD+) when they are confluent with respect to when they are isolated.

5) Wnt signaling is found to contribute to the colon cancer cell phenotype through regulation of cancer cell metabolism. dnLEF-1 inhibits colon cancer cell phenotype and shift the metabolism from glycolysis to oxidative phosphorylation.

6) Different compartments of the small intestine tissue are found to be characterized by unique Phasor FLIM signatures. We can distinguish collagen fibers at the base of the crypts, the lamina propria, the vascular network and the epithelium.

7) Stem cells at the small intestine crypt base were found to have a lower redox ratio with respect to the Paneth cells.

8) Stem cells in the small intestine have been label-free, non-invasively identified and imaged in vivo, under physiologic conditions.

9) Epithelial cells in the small intestine were found to have a metabolic shift during differentiation. Stem cells at the base of the crypt have the shortest lifetime and the highest NADH/NAD+ ratio. Movement up the crypt to transit amplifying cells and fully differentiated cells on the mucosal surface corresponds to different FLIM signatures that correspond to decreasing NADH/NAD+ ratios.

10) The nuclei of cells have been found to have a higher free/bound NADH ratio with respect to the mitochondria and cell cytoplasm.

11) The nuclei of cells have been found to have a heterogeneous distribution of the free/bound NADH that might be indicative of the transcriptional map in the nucleus.

12) After the addition of potassium cyanide (KCN) to the cells, to block oxidative phosphorylation during cellular respiration, the concentration of free NADH has been observed to increase 13) Two intrinsic optical biomarkers have been identified to define the differentiation status of human embryonic stem cells (hESCs): NADH and lipid droplet-associated granules (LDAGs).

14) Lipid droplet-associated granules (LDAGs) in human embryonic stem cells (hESCs) are found to have a unique long lifetime signature and are found to have a function in protein aggregates, oxidized lipids and damaged organelles storage.

15) During early hESC differentiation the concentration of NADH has been found to increase while the concentration of LDAGs decreases. Hence hESC differentiation has been found to be characterized by a decrease in oxidative phosphorylation rate and concentration of fluorescent proteins modified, by reactive oxygen species (ROS).

16) Higher metabolic heterogeneity is found in differentiating H9 hESC colonies with respect to undifferentiated H9 hESC colonies 17) Higher metabolic heterogeneity has been found in H1 hESCs colonies with respect to H9 hESC colonies.

18) Neuronal stem/progenitor cells (NSPCs) have been found to have a higher redox ratio (NADH/NAD+) with respect to the differentiated neurons.

19) NSPCs from earlier (E12-mostly committed to a neuronal fate) developmental time points have higher redox ratio with respect to NSPCs from later (E16—mostly committed to a glial fate) developmental time points.

Materials and Methods

Tissue and Solution Preparation.

Seminiferous Tubules

One year old mice expressing green fluorescent protein (GFP) from an Oct4 transgene were scarified. Seminiferous tubules are extracted from the testes and mounted between cover slip in PBS medium. Fresh tissues are imaged within two hours from the extraction.

*C. Elegans* Germline

We used the strain of *C. elegans* with histone tagged with gfp. The samples were maintained at 20° C. Germ cell differentiation state within the *C. elegans* was estimated by looking at the shape of the nuclei and by counting rows from the distal tip cell.

Animal Protocols were approved by IACUC.

Small Intestine and Colon Imaging

For live crypt imaging, 4-6 week old Lgr5+ mice is be fasted for 24 hours prior to being anesthetized with 0.4 cc of ketamine-xylazine given IP, and immobilized (with clear tape) on their side on a glass slide. A 1 cm vertical incision will be made 0.5 cm to the left of midline of the abdomen and a loop of small bowel exteriorized. The loop will be placed on the surface of the glass slide, with a minimal volume of PBS to prevent desiccation of the serosal surface. The prepared animal will be placed on the stage of the microscope and imaged. A long-working length objective (40×, 0.8 NA with 2 mm working distance) is used to focus in tissue planes within loops of small intestine and colon. At the end of the imaging session, mice will be euthanized with an overdose of ketamine.

Colon Cancer Cells

Formation of stable cell lines that inducibly express dnLEF-1:DLD1 TR7 cells (DLD1 colon cancer cells expressing Tet repressor; generous gift from M. van de Wetering and H. Clevers) were transfected with a vector for Tet inducible dnLEF-1N (2 g) by Effectene transfection reagent (QIAGEN). Stably transfected cells were selected in complete RPMI media containing 500 ug/ml Zeocin (InvivoGen) and 10 µg/ml Blasticidin (InvivoGen) and those cells that were resistant to Zeocin and Blasticidin were isolated as single colonies. These clonal cells were expanded into individual cell lines and screened for the highest levels of induced dnLEF-1N protein expression by Western blot analysis.

Induction of dnLEF-1:

Stable DLD1 cells that inducibly express dnLEF-1 were seeded at a density of 150,000 cells per 9 cm2 and were grown in complete RPMI in the absence of selection antibiotics. Doxycycline (0.01 µg/ml) was added at the time of seeding to induce dnLEF-1 expression. An equal amount of water was added to a matching "mock" plate. These plates were monitored by FLIM analysis over a five to six day period after seeding, comparing the mock treated (−dnLEF-1) to the doxycycline treated (+dnLEF-1) cells. Cells were maintained at 37° C. in-between imaging and the media was replaced daily (supplemented with water or doxycycline).

Human Embryonic Stem Cells Culture:

We used federally approved H9 and H1 human embryonic stem cell lines. hESCs are cultured on a substrate of mouse fibroblast (MEFs) feeders (Chemicon Cat# PMEF-CF). Plates are first coated with 0.1%-0.2% gelatin (Sigma #G-1393). MEFs are then plated with a density of approximately of 15000 cells per cm2. hESCs ranging from passage 44 to 56 were used for image analysis. hESCs were grown in hESC culture medium: DMEM-F12 (Invitrogen 12660), 20% Knokcout serum replacement (KOSR, Invitrogen 10828), 1% non essential amino acids (NEAA, Invitrogen 11140-050), 1 mM Glutamax (Invitrogen 35035), 4 ng/mL basic fibroblast growth factors (bFGF, Invitrogen 13256-029) and 0.1 mM beta-mercaptoetanol. Differentiation was induced by removing bFGF from hESC medium and adding either 100 ng/ml BMP4 (R&D) or Retinoic acid (1 uM). hESCs are differentiated for four days before they are imaged. MEFs medium: Dulbecco's Modified Eagle Medium (DMEM), 1 mM Glutamax (Invitrogen 10569), 10% Fetal Bovine Serum (FBS Invitrogen 16000-044) and 1% non-essential amino acids (Invitrogen 11149-035).

In Vivo Staining:

Lipid droplets were stained with BODIPY 493/503 (Invitrogen #D3922). hESCs mitochondria were stained with 1 ul/1 ml TMRE (Tetramethylrhodamine ethyl ester perchlorate, Sigma #87917 Excitation/Emission 540/595 nm) solution. After 30 min of staining cells were washed and imaged. hESCs lysosomes were stained with 50 nM LysoTracker Red (Invitrogen L7528, Excitation/Emission:577/590 nm) in PBS. Endoplasmic Reticulum was stained with ER-Tracker™ Red (Invitrogen #E34250).

KCN Treatment

We block the respiratory chain by means of potassium cyanide (KCN) to inhibit the Oxidative phosphorylation and increase the mitochondrial concentration of NADH. KCN in PBS was added to the culture medium with a final concentration of 4 mM. Cells were imaged immediately after the addition of KCN.

Immunostaining

Medium was removed from the stem cell plate and washed with PBS. Cells were fixed in 4% PFA. hESCs were washed 3 times with PBS, permeabilized with 1 ml cold Methanol for 5 minutes at room temperature and then washed 3 times with PBS. The cells were blocked for an hour at room temperature using 10% Donkey serum (Sigma D9663) in PBS. Primary antibodies, OCT4 (R&D AF1759—1:100) and CONNEXIN-43 (Cell Signaling 3512—1:50) were diluted in 1% Donkey serum and incubated with the cells for an hour at room temperature. Cells are washed 3 times. with PBS. The secondary antibody Donkey anti-Goat Alexa 568 (Invitrogen A-11057) was used at a 1:400 and incubated with the hESCs for one hour at room temperature. Dapi solution is added to the cell to stain DNA. Finally cells are washed with PBS.

Mouse Neuronal Stem/Progenitor Cell Primary Culture

Mouse fetal-derived NSPCs were cultured from cerebral cortical regions of wild-type CD1 mice at embryonic days 12 and 16 (E12 and E16). Cultures of NSPCs were grown as neurospheres in Dulbecco's modified Eagle's medium, B27, N2, 1 mM sodium pyruvate, 2 mM glutamine, 1 mM N-acetylcysteine (Sigma-Aldrich, St. Louis, on the world wide web at sigmaaldrich.com), 20 ng/ml epidermal growth factor (BD Biosciences, Bedford, Mass., on the world wide web at bdbiosciences.com), 10 ng/ml fibroblast growth factor (BD Biosciences), and 2 g/ml heparin (Sigma-Aldrich) (all culture reagents from Gibco [Grand Island, N.Y., on the world wide web at invitrogen.com] unless otherwise specified). Neurospheres are a heterogeneous collection of cells that includes a small number of stem cells, a greater number of more specified progenitor cells, and a few differentiated cells. For differentiation, neurospheres were dissociated, and cells were plated on laminin-coated coverslips in medium lacking growth factors and heparin. Neurons and astrocytes from E12.5 mouse cortices were cultured on coverslips coated with Matrigel (BD Biosciences) using medium described previously. Neurons were cultured for 2 days prior to analysis.

Retinol solution (Retinol all trans, Sigma no. R7632) was prepared in DMSO at a concentration of 1 mg/ml at pH 8.5. Retinoic acid (Sigma no. R2625) solution was prepared in DMSO at a concentration of 0.01M (3 mg/ml) at pH 8.5. 250 µM NADH (Sigma n.N8129) solution was prepared in 100 mM Mops buffer at pH 7. A solution of 250 µM NADH is mixed 1:1 with 1000 unit/ml lactate dehydrogenase (LDH, Sigma no. L3916). A solution of 250 µM NADH is mixed 5:1 with ~700 units/mg protein of malate dehydrogenase (MDH, Sigma no. M1567). FAD (Sigma n.F6625) is diluted at 2 mg/ml in water at pH 7.4. GFP is diluted in 10 mM Tris buffer at a concentration of 20 nM. Protoporphyrin IX (Sigma P8293) is diluted at 1.5 mg/ml in dimethylformamide:methanol (1:1) at pH 7. The phasor location of GFP and collagen were measured at 900 nm. The phasors of retinol, retinoic acid, NADH and FAD were measured at 760 nm and of porphyryn IX was measured at 790 nm wavelength. Collagen matrix is prepared with Collagen Type I (BD Biosciences 354236) at a concentration of 3.75 mg/ml.

Imaging.

Fluorescence lifetime images are acquired with two different microscopes. The first set up is a two-photon microscope coupled with a Becker and Hickl 830 card (Becker adn Hickl, Berlin). Ti:Sapphire laser system (Spectra-Physics Mai Tai) with 80 MHz repetition rate is used to excite the sample. The laser is coupled with an Zeiss Axiovert S100TV microscope. The scanning system is constituted by a scanning mirror (Cambridge Technology Mirror scanner 6350). A Zeiss 40×1.2 NA water immersion objective is used. For image acquisition the following settings are used: image size of 256×256 pixels, scan speed of 32 µm/pixel. A dichroic filter (700DCSPXR, Chroma Technologies) is used to separate the fluorescence signal from the laser light and the fluorescence is detected by a hybrid detector (HPM-100 of Hamamatsu). An additional barrier filter is used to block the near IR light. The second set up for FLIM is a Zeiss 710 microscope coupled to a Ti:Sapphire laser system (Spectra-Physics Mai Tai) and a ISS A320 FastFLIM (Colyer 2008). A 40×1.2 NA water immersion objective (Zeiss Korr C-Apochromat) is used. For image acquisition the following settings are used: image size of 256×256 pixels or 1024v1024 pixels and scan speed of 25 µm/pixel. A dichroic filter (690 nm) is used to separate the fluorescence signal from the laser light and the fluorescence. For the acquisition of FLIM images, fluorescence is detected by a photomultiplier (H7422P-40 of Hamamatsu) and a 610 nm short pass filter is placed in front of the detector. FLIM data are acquired and processed by the SimFCS software developed at the Laboratory of fluorescence dynamics. The excitation wavelengths used were 900 nm, 880 nm and 740 nm. All samples are excited at 900 nm if not differently specified. An average power of about 5 mW was used to excite the live tissue. FLIM calibration of the system is performed by measuring the known lifetime of the fluorescein with a single exponential of 4.04 ns. FLIM data are collected until 100 counts in the brightest pixel of the image are acquired. Typically the acquisition time was of the order of few seconds.

Data Analysis.

Every pixel of the FLIM image is transformed in one pixel in the phasor plot. The components g (x-coordinate) and s (y-coordinate) of the phasor plot are respectively the real and imaginary part of the Fourier transform of the fluorescence impulse response. The coordinates g and s in the phasor plot are calculated from the fluorescence intensity decay of each pixel of the image by using the transformations defined in equations 1 and 2.

$$g_{i,j}(\omega) = \frac{\int_0^\infty I_{i,j}(t)\cos(\omega t)\,dt}{\int_0^\infty I_{i,j}(t)\,dt} \quad (1)$$

-continued $$s_{i,j}(\omega) = \frac{\int_0^\infty I_{i,j}(t)\sin(\omega t)\,dt}{\int_0^\infty I_{i,j}(t)\,dt} \qquad (2)$$

where the indices i and j identify a pixel of the image and ω is the laser frequency (ω=2πf). f is the laser repetition rate, i.e. 80 MHz. All phasor plots are transformed at 80 MHz, i.e. the first harmonic of the laser repetition rate, if not differently specified. The analysis of the phasor distribution is performed by cluster identification. Clusters of pixel values are detected in specific regions of the phasor plot. The cluster assignment is performed by taking in account not only the similar fluorescence properties in the phasor plot but also exploiting the spatial distribution and localization in cellular substructures or tissues. We achieve this by applying a median filter that imposes a correlation between cluster of pixels in the phasor plot and pixels of the image without decreasing the spatial resolution. This allows better confining a cluster to a specific phasor value, by reducing the statistical error in the phasor associated with each pixel of the image. Regions of the image with different decay profiles and characteristics can be better delineated. In order to obtain information on the chemical composition of tissues, we compare the size of their phasor distribution with the statistical uncertainty, which depends on the inverse of the square-root of the number of photons collected. If the size of the phasor distribution is comparable to the statistical uncertainty, we select an independent molecular species using a circular selection cursor. If the phasor distribution size is greater than the statistical uncertainty we select a mixture of molecular components using a cursor which joins the two molecular species. Fractional intensities of chemical species in every pixel of the image are evaluated with a graphical analysis in the phasor plot (See Supplementary Materials). We perform Image segmentation on the FLIM data by selecting the region of interest of germ cells within the tissue. The region of interest of cells is selected by using a circular cursor of 5 μm diameter. We calculate the phasor average value within these regions of interest. All phasor transformation and the data analysis of FLIM data are performed using SimFCS software developed at the LFD.

Supplementary Materials

For FIGS. SM1-SM5 that are now described see FIGS. 6-9, respectively.

The Phasor Transformation and Resolution of a Mixture of Components

The phasor transformations of FLIM data acquired in the frequency domain at an angular modulation frequency ω are:

$$g_{i,j}(\omega) = m_{i,j} \cos \varphi_{i,j} \qquad (1)$$

$$s_{i,j}(\omega) = m_{i,j} \sin \varphi_{i,j} \qquad (2)$$

where $m_{i,j}$ and $\varphi_{i,j}$ are the modulation and the phase of the emission with respect to the excitation. Estimations of the lifetime in terms of the phase and modulation can be performed in each pixel by the following formulas [56, 57]:

$$\tau_\varphi = \frac{1}{\omega}\tan(\varphi) \qquad (3)$$

$$\tau_m = \frac{1}{\omega}\sqrt{\left(\frac{1}{m^2}-1\right)} \qquad (4)$$

In the case of a single exponential the two separate lifetimes obtained by the phase and by the modulation with equation (3) and (4) are equal, while for a multi exponential lifetime system the apparent lifetimes are different.

In the phasor plot if the decay is a single exponential $I(t)=Ae^{-t/\tau}$ the coordinates are given by:

$$g(\omega) = \frac{1}{1+(\omega\tau)^2} \qquad (5)$$

$$s(\omega) = \frac{\omega\tau}{1+(\omega\tau)^2} \qquad (6)$$

Where τ is the lifetime of the decay and ω is the laser frequency. There is a direct relationship between a phasor point and lifetime. Every possible lifetime can be mapped into this universal representation of the decay (phasor plot). All possible single exponential lifetimes lie on the "universal circle" defined as the semicircle going from point (0, 0) to point (1, 0) with radius ½. Point (1, 0) corresponds to τ=0, while point (0, 0) to τ=∞. In the phasor coordinates the single lifetime components add directly because the phasor follows the vector algebra. A mixture of two distinct single lifetime components, each of which lie separately on the single lifetime semicircle, does not lie on the semicircle. All the composition of two single exponential components must be along the line joining the two lifetime points. In a system with many single lifetime components the phasor coordinate g and s are described as:

$$g(\omega) = \sum_k \frac{h_k}{1+(\omega\tau_k)^2} \qquad (7)$$

$$s(\omega) = \sum_k \frac{h_k \omega\tau_k}{1+(\omega\tau_k)^2} \qquad (8)$$

where $h_k$ is the intensity weighted fractional contribution of the single-exponential component with lifetime $\tau_k$. The phasor location of the mixture of single-lifetimes is the intensity-weighted average of the contributions of each single-lifetime that lie separately on the semicircle.

In general in a system with multiple fluorescent components like a tissue the overall decay is a phasor that is the sum of the independent phasors of each fluorescence component:

$$G(\omega) = \sum_n f_n g_n(\omega) \qquad (9)$$

$$S(\omega) = \sum_n f_n s_n(\omega) \qquad (10)$$

Where $f_n$ is the fractional contribution of each component characterized by the phasor coordinates $g_n$ and $s_n$. Two molecular species with multi-exponential decay are identified by two specific points in the phasor plot inside the semicircle. All possible weighting of the two molecular species give phasors distributed along a straight line joining the phasors of the two species. In the case of three molecular species, all the possible combinations are contained in a triangle where the vertices correspond to the phasor of the pure species. The phasor plot of an N-component mixture will be contained in a polygon with N-vertices located in the position of the phasor of each contributing component. The calculation of the fractional intensities $f_n$ of different fluorescence components that contribute to the signal is performed by a linear estimation on the system described by equation (9) and (10) by graphically resolving the sum of phasors.

Multiple Harmonic Phasor Analysis

Phasor transformation of data both acquired in the time domain or frequency domain can be performed at higher harmonics of the fundamental laser frequency ω. We analyze the same FLIM data with phasor transformations at the second and third harmonic ($\omega=n\omega_o$ with n=2, 3) of the fundamental laser repetition angular frequency ($\omega_o=2\pi f$), where f is the laser repetition rate, i.e. 80 MHz. For each frequency at which the FLIM data are transformed we obtain a different phasor histogram. Multi harmonic phasor analysis of FLIM images can separate tissue components that have a similar phasor location but arise from different lifetime distribution as FIGS. SM3 and SM4 show. The sensitivity of components separation with higher harmonics analysis is greater for the short lifetime component such as collagen.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

REFERENCES

All references disclose herein are incorporated by reference in their entirety

Alcala, J. R., Gratton, E., Prendergast, F. G. (1987). "Fluorescence lifetime distributions in proteins." *Biophys J.* 51(4): 597-604.

Bel'Kov, M. V. B., S. L. (1990). "Fluorescence spectra and kinetics of isomers and dimers of retinoic acid." *Journal of Applied Spectroscopy* 53(6): 1271-1275.

Bornstein, P., Kang, A. H., Piez, K. A. (1966). "The nature and location of intramolecular cross-links in collagen." *Proc Natl Acad Sci USA* 55(2):(2): 417-24.

Bowles, J., Knight, D., Smith, C., Wilhelm, D., Richman, J., Mamiya, S., Yashiro, K., Chawengsaksophak, K., Wilson, M. J., Rossant, J., Hamada, H., Koopman, P. (2006). "Retinoid signaling determines germ cell fate in mice." *Science* 312(5773): 596-600.

Brancaleon, L., Magennis, S. W., Samuel, I. D., Namdas, E., Lesar, A., Moseley, H. (2004). "Characterization of the photoproducts of protoporphyrin IX bound to human serum albumin and immunoglobulin" *G. Biophys Chem.* 109(3): 351-60.

Campagnola, P. J., Loew, L. M. (2003). "Second-harmonic imaging microscopy for visualizing biomolecular arrays in cells, tissues and organisms." *Nat. Biotechnol.* 21(11): 1356-60.

Chia, T. H., Williamson, A., Spencer, D. D., Levene, M. J. (2008). "Multiphoton fluorescence lifetime imaging of intrinsic fluorescence in human and rat brain tissue reveals spatially distinct NADH binding." *Opt Express.* 16(6): 4237-49.

Cinquin, O., Crittenden, S. L., Morgan, D. E., Kimble (2010). "Progression from a stem cell-like state to early differentiation in the C. elegans germ line." *Proc Natl Acad Sci USA.* 107(5): 2048-53.

Clayton, A. H., Hanley, Q. S., Verveer, P. J. (2004). "Graphical representation and multicomponent analysis of single-frequency fluorescence lifetime imaging microscopy data." *J. Microsc.* 213(Pt 1): 1-5.

Colyer, R., Lee, C., Gratton, E. (2008). "A novel fluorescence lifetime imaging system that optimizes photon efficiency." *Microsc Res Tech.* 71(3): 201-13.

Denk, W., Strickler, J. H., Webb, W, W. (1990). "Two-photon laser scanning fluorescence microscopy." *Science* 248 (4951): 73-6.

Digman, M. A., Caiolfa, V. R., Zamai, M., Gratton, E. (2008). "The phasor approach to fluorescence lifetime imaging analysis." *Biophys J.* 94(2): L14-6.

Durston, A. J., Timmermans, J. P., Hage, W. J., Hendriks, H. F., de Vries, N. J., Heideveld, M., Nieuwkoop, P. D. (1989). "Retinoic acid causes an anteroposterior transformation in the developing central nervous system." *Nature* 340(6229): 140-4.

Guo, H. W., Chen, C. T., Wei, Y. H., Lee, O. K., Gukassyan, V., Kao, F. J., Wang, H. W. (2008). "Reduced nicotinamide adenine dinucleotide fluorescence lifetime separates human mesenchymal stem cells from differentiated progenies." *J Biomed Opt.* 13(3): 050505.

Helmchen, F., Denk, W. (2005). "Deep tissue two-photon microscopy." *Nat. Methods.* 2(12): 932-40.

Hess, S. T., Sheets, E. D., Wagenknecht-Wiesner, A., Heikal, A. A. (2003). "Quantitative analysis of the fluorescence properties of intrinsically fluorescent proteins in living cells." *Biophys J.* 85(4): 2566-80.

Huang, S., Heikal, A. A., Webb, W. W. (2002). "Two-photon fluorescence spectroscopy and microscopy of NAD(P)H and flavoprotein." *Biophys J.* 82(5): 2811-2825

Jameson, D. M., Gratton., E., Hall, R. D. (1984). "The Measurement and Analysis of Heterogeneous Emissions by Multifrequency Phase and Modulation Fluorometry." *Applied Spectroscopy Reviews* 20(1): 55-106.

König, K., Riemann, I. (2003). "High-resolution multiphoton tomography of human skin with subcellular spatial resolution and picosecond time resolution." *J Biomed Opt.* 8(3): 432-9.

König, K., Uchugonova, A., Gorjup, E. (2010). "Multiphoton fluorescence lifetime imaging of 3D-stem cell spheroids during differentiation." *Microscopy Research and Technique* 00: 000-000

Lakowicz, J. R., Szmacinski, H., Nowaczyk, K., Johnson, M. L. (1992). "Fluorescence lifetime imaging of free and protein-bound NADH." *Proc Natl Acad Sci USA.* 89(4): 1271-5.

Lin, Y., Gill, M. E., Koubova, J., Page, D. C. (2008). "Germ cell-intrinsic and -extrinsic factors govern meiotic initiation in mouse embryos." *Science* 322(5908): 1685-7.

Lonergan, T., Brenner, C., Bavister, B. (2006). "Differentiation-related changes in mitochondrial properties as indicators of stem cell competence." *J Cell Physiol.* 208(1): 149-53.

Medine, C. N., McDonald, A., Bergmann, A., Duncan, R. R. (2007). "Time-correlated single photon counting FLIM: some considerations for physiologists." *Microsc Res Tech.* 70(5): 420-5.

Parker, G. C., Acsadi, G., Brenner, C. A. (2009). "Mitochondria: determinants of stem cell fate?." *Stem Cells Dev.* 18(6): 803-6.

Pelet, S., Previte, M. J., Laiho, L. H., So, P. T. (2004). "A fast global fitting algorithm for fluorescence lifetime imaging microscopy based on image segmentation." *Biophys J.* 87(4): 2807-17.

Peter, M., Ameer-Beg, S. M. (2004). "Imaging molecular interactions by multiphoton FLIM." *Biol Cell.* 96(3): 231-6.

Redford, G. I., Clegg, R. M. (2005). "Polar plot representation for frequency-domain analysis of fluorescence lifetimes." *J. Fluoresc.* 15(5): 805-15.

Schneckenburger, H., Wagner, M., Weber, P., Strauss, W. S., Sailer, R. (2004). "Autofluorescence lifetime imaging of cultivated cells using a UV picosecond laser diode." *J Fluoresc.* 14(5): 649-54.

Skala, M. C., Riching, K. M., Gendron-Fitzpatrick, A., Eickhoff, J., Eliceiri, K. W., White, J. G., Ramanujam, N. (2007). "In vivo multiphoton microscopy of NADH and FAD redox states, fluorescence lifetimes, and cellular morphology in precancerous epithelia." *Proc Natl Acad Sci USA* 104(49): 19494-9.

Smith, J., Ladi, E., Mayer-Proschel, M., Noble, M. (2000). "Redox state is a central modulator of the balance between self-renewal and differentiation in a dividing glial precursor cell." *Proc Natl Acad Sci USA* 97(18): 10032-7.

Squirrell, J. M., Wokosin, D. L., White, J. G., Bavister, B. D. (1999). "Long-term two-photon fluorescence imaging of mammalian embryos without compromising viability." *Nat. Biotechnol.* 17(8): 763-7.

Uchugonova, A., König, K. (2008). "Two-photon autofluorescence and second-harmonic imaging of adult stem cells." *J Biomed Opt.* 13(5): 054068.

Verveer, P. J., Squire, A., Bastiaens, P. I. (2000). "Global analysis of fluorescence lifetime imaging microscopy data." *Biophys J.* 78(2127-37).

Wouters, F. S., Verveer, P. J., Bastiaens, P. I. (2001). "Imaging biochemistry inside cells." *Trends Cell Biol.* 11(5): 203-11.

Zipfel, W. R., Williams, R. M., Christie, R., Nikitin, A. Y., Hyman, B. T., Webb, W. W. (2003). "Live tissue intrinsic emission microscopy using multiphoton-excited native fluorescence and second harmonic generation." *Proc Natl Acad Sci USA* 100(12): 7075-80

Zipfel, W. R., Williams, R. M., Webb, W. W. (2003). "Nonlinear magic: multiphoton microscopy in the biosciences." *Nat. Biotechnol.* 21(11): 1369-77.

Becker, W., Bergmann, A., Hink, M. A., König, K., Benndorf, K., Biskup, C. (2004). "Fluorescence lifetime imaging by time-correlated single-photon counting." *Microsc Res Tech.* 63(1): 58-66.

Chorvat, D., Jr., Chorvatova, A. (2009). "Multi-wavelength fluorescence lifetime spectroscopy: a new approach to the study of endogenous fluorescence in living cells and tissues." *Laser Physics Letters* 6(3): 175-193.

Dabir, A., Trivedi, C A., Ryu, Y., Pande, P., Jo, J A. (2009). "Fully automated deconvolution method for on-line analysis of time-resolved fluorescence spectroscopy data based on an iterative Laguerre expansion technique." *J Biomed Opt* 14(2):024030.

Fu, Ng, B K, Razul, S G. (2009). "Fluorescence lifetime discrimination using expectation-maximization algorithm with joint deconvolution." *J Biomed Opt.* 14(6): 064009.

Jo, J. A., Fang, Q., Papaioannou, T., Marcu, L. (2004). "Fast model-free deconvolution of fluorescence decay for analysis of biological systems." *Journal of Biomedical Optics* 9(4): 743-752.

Lee, K., Siegel, J, Webb, S E, Leveque-Fort, S, Cole, M J, Jones, R, Dowling, K, Lever, M J, French, P M. (2001). "Application of the stretched exponential function to fluorescence lifetime imaging." *Biophys J.* 81(3): 1265-74.

Munro, I., McGinty, J, Galletly, N, Requejo-Isidro, J, Lanigan, P M, Elson, D S, Dunsby, C, Neil, M A, Lever, M J, Stamp, G W, French, P M. (2005). "Toward the clinical application of time-domain fluorescence lifetime imaging." *J Biomed Opt.* 10(5): 051403.

Pelet, S., Previte, M J, Laiho, L H, So, P T. (2004). "A fast global fitting algorithm for fluorescence lifetime imaging microscopy based on image segmentation." *Biophys J.* 87(4): 2807-17.

Siegel J, E. D., Webb S E, Lee K C, Vlandas A, Gambaruto G L, Lévêque-Fort S, Lever M J, Tadrous P J, Stamp G W, Wallace A L, Sandison A, Watson T F, Alvarez F, French P M. (2003). "Studying biological tissue with fluorescence lifetime imaging: microscopy, endoscopy, and complex decay profiles." *Appl Opt.* 42(16): 2995-3004.

The invention claimed is:

1. A method for discriminating the metabolic state of cells with in vivo measurements in a metabolically active in vivo tissue which is part of a living mammalian individual, comprising using a fluorescence lifetime imaging microscope apparatus that acquires fluorescence lifetime imaging microscopy (FLIM) data from fluorescence signals of the in vivo tissue; and using an electronic circuit configured to apply fluorescence lifetime imaging to an autofluorescence signal of the tissue and thereby acquire autofluorescence FLIM data, wherein the electronic circuit is configured to
i) receive information identifying at least two selected cells of the tissue,
ii) calculate an average autofluorescence phasor value for a region of each selected cell based on phasor values determined from autofluorescence FLIM data for each selected cell, and
iii) generate a scatterplot representing redox states of the selected cells based on the average autofluorescence phasor values.

2. The method of claim 1, wherein the electronic circuit is configured to calculate a relative concentration of a tissue or cell component based on the fluorescence lifetime imaging microscopy data.

3. The method of claim 1, wherein the electronic circuit is configured to monitor metabolic changes of cells that occur after (a) drug interaction, (b) oxidative stress, (c) differentiation, or (d) carcinogenesis.

4. The method of claim 1, wherein the electronic circuit is configured to detect differences in redox ratios of cells in the tissue.

5. The method of claim 1, wherein the system is able to perform high throughput screening to detect precancer stages and perform early diagnosis in an individual.

6. The method of claim 1, wherein the electronic circuit is configured to perform multi-harmonic analysis of the fluorescence lifetime imaging data using higher harmonics of laser repetition rate.

7. The method of claim 1, wherein the autofluorescence signal is from NADH.

8. The method of claim 1, wherein the autofluorescence signal is from NADH, FAD and/or another flavin.

\* \* \* \* \*